(12) United States Patent
Andrés-Gil et al.

(10) Patent No.: US 8,852,554 B2
(45) Date of Patent: Oct. 7, 2014

(54) RADIOLABELLED PDE10 LIGANDS

(75) Inventors: José Ignacio Andrés-Gil, Madrid (ES); Meri De Angelis, Toledo (ES); Guy Maurits R. Bormans, Rotselaar (BE); Sofie Jeanne Leopoldine Celen, Tessenderlo (BE)

(73) Assignee: Janssen Pharmaceutica NV, Beerse (BE)

( * ) Notice: Subject to any disclaimer, the term of this patent is extended or adjusted under 35 U.S.C. 154(b) by 135 days.

(21) Appl. No.: 13/505,157

(22) PCT Filed: Oct. 27, 2010

(86) PCT No.: PCT/EP2010/066237
§ 371 (c)(1),
(2), (4) Date: Apr. 30, 2012

(87) PCT Pub. No.: WO2011/051324
PCT Pub. Date: May 5, 2011

(65) Prior Publication Data
US 2012/0213703 A1    Aug. 23, 2012

(30) Foreign Application Priority Data
Oct. 30, 2009 (EP) .................................... 09174702

(51) Int. Cl.
*A61K 51/04* (2006.01)
*C07D 401/14* (2006.01)

(52) U.S. Cl.
CPC .......... *C07D 401/14* (2013.01); *A61K 51/0455* (2013.01)
USPC ....................... 424/1.89; 424/1.85; 424/9.351

(58) Field of Classification Search
USPC .............. 424/1.85, 1.89, 9.351; 548/200, 448
See application file for complete search history.

(56) References Cited

FOREIGN PATENT DOCUMENTS

| WO | 2006/072828 | 7/2006 |
|---|---|---|
| WO | WO 2006/072828 | 7/2006 |
| WO | 2007/129183 | 11/2007 |
| WO | WO 2007/129183 | 11/2007 |
| WO | 2010/097367 | 9/2010 |

OTHER PUBLICATIONS

C.J. Schmidt et al. Preclinical Characterization of Selective Phosphodiesterase 10A Inhibitors: a new Therapeutic Approach to the Treatment of Schizophrenia, The Journal of Pharmacology and Experimental Therapeutics, 325, 681-690, 2008.*
Schmidt C J et al., Journal of Pharmacology and Experimental Therapeutics, American Society for Pharmacology and Experimental Therapeutics, vol. 325, No. 2, XP002534689.
Verhoest P R et al., Journal of Medicinal Chemistry, American Chemical Society, vol. 52, No. 16 XP002567796.
International Search Report for PCT/EP2010/066237 dated Mar. 10, 2011.
Schmidt C J et al., Journal of Pharmacology and Experimental Therapeutics, American Society for Pharmacology and Experimental Therapeutics, vol. 325, No. 2, XP002534689, pp. 681-690, 2008.
Verhoest P R et al., Journal of Medicinal Chemistry, American Chemical Society, vol. 52, No. 16 XP002567796, pp. 5188-5196, 2009.
Bonner et al., Bioorganic & Medicinal Chemistry 18 (2010) 6763-6770.
Tu et al., Nuclear Medicine and Biology 37 (2010) 509-516.

* cited by examiner

*Primary Examiner* — Michael G Hartley
*Assistant Examiner* — Jagadishwar Samala
(74) *Attorney, Agent, or Firm* — Hal B. Woodrow

(57) ABSTRACT

The present invention relates to novel, selective, radiolabelled PDE10 ligands which are useful for imaging and quantifying the PDE10A enzyme in tissues, using positron-emission tomography (PET). The invention is also directed to compositions comprising such compounds, to processes for preparing such compounds and compositions, and to the use of such compounds and compositions for imaging a tissue, cells or a host, in vitro or in vivo.

7 Claims, No Drawings

RADIOLABELLED PDE10 LIGANDS

CROSS REFERENCE TO RELATED APPLICATIONS

This application is the national stage of PCT Application No. PCT/EP2010/066237, filed Oct. 27, 2010, which claims priority from European Patent Application No. 09174702.2, filed Oct. 30, 2009, the entire disclosures of which are hereby incorporated in their entirety.

FIELD OF THE INVENTION

The present invention relates to novel, selective, radiolabelled PDE10 ligands which are useful for imaging and quantifying the PDE10A enzyme in tissues, using positron-emission tomography (PET). The invention is also directed to compositions comprising such compounds, to processes for preparing such compounds and compositions, and to the use of such compounds and compositions for imaging a tissue, cells or a host, in vitro or in vivo.

BACKGROUND OF THE INVENTION

Phosphodiesterases (PDEs) are a family of enzymes encoded by 21 genes and subdivided into 11 distinct families according to structural and functional properties. These enzymes metabolically inactivate widely occurring intracellular second messengers, 3',5'-cyclic adenosine monophosphate (cAMP) and 3',5'-cyclic guanosine monophosphate (cGMP). These two messengers regulate a wide variety of biological processes, including pro-inflammatory mediator production and action, ion channel function, muscle contraction, learning, differentiation, apoptosis, lipogenesis, glycogenolysis, and gluconeogenesis. They do this by activation of protein kinase A (PKA) and protein kinase G (PKG), which in turn phosphorylate a wide variety of substrates including transcription factors and ion channels that regulate innumerable physiological responses. In neurons, this includes the activation of cAMP and cGMP-dependent kinases and subsequent phosphorylation of proteins involved in acute regulation of synaptic transmission as well as in neuronal differentiation and survival. Intracellular concentrations of cAMP and cGMP are strictly regulated by the rate of biosynthesis by cyclases and by the rate of degradation by PDEs. PDEs are hydrolases that inactivate cAMP and cGMP by catalytic hydrolysis of the 3'-ester bond, forming the inactive 5'-monophosphate (Scheme 1).

Scheme 1

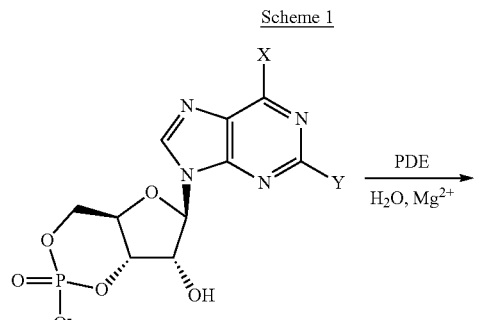

cAMP X = NH$_2$, Y = H
cGMP X = O, Y = NH$_2$

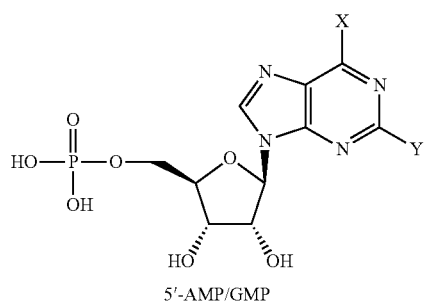

5'-AMP/GMP

On the basis of substrate specificity, the PDE families can be divided into three groups: i) the cAMP-specific PDEs, which include PDE4, -7 and -8; ii) the cGMP-selective enzymes PDE5 and -9; and iii) the dual-substrate PDEs, PDE1, -2 and -3, as well as PDE10 and -11. The discovery of phosphodiesterase 10A (PDE10A) was reported in 1999. Of all the 11 known PDE families, PDE10A has most restricted distribution with high expression only in the brain and testes. In the brain, PDE10A mRNA and protein are highly expressed in the striatum. This unique distribution of PDE10A in the brain, together with its increased pharmacological characterization, points to the potential use of PDE10A inhibitors for treating neurological and psychiatric disorders like schizophrenia.

Positron Emission Tomography (PET) is a non-invasive imaging technique that offers the highest spatial and temporal resolution of all nuclear imaging techniques and has the added advantage that it can allow for true quantification of tracer concentrations in tissues. It uses positron emitting radionuclides such as, for example, 15O, $^{13}$N, $^{11}$C and $^{18}$F for detection.

WO-2006/072828 (Pfizer) discloses heteroaromatic quinoline compounds as selective PDE10 inhibitors. WO-2007/129183 (Pfizer) discloses bicyclic heteroaryl compounds as PDE10 inhibitors.

Zhude Tu et al. disclose [$^{11}$C]-papaverine as a PET tracer for imaging PDE10A (Nuclear Medicine and Biology, 37, 509-516, 2010) and conclude that it is not an ideal radioligand for clinical imaging of PDE10A in the central nervous system. It is opined that analogues are required having higher selectivity for PDE10A over PDE3 and improved pharmacokinetic properties.

WO-2010/097367 discloses radiolabelled quinoline compounds, e.g. -2-{4-[1-(2-[$^{18}$F]fluoroethyl)-4-pyridin-4-yl-1H-pyrazol-3-yl]-phenoxymethyl}-quinoline, useful as PDE10A ligands.

SUMMARY OF THE INVENTION

The present invention relates to a compound having the Formula (I)

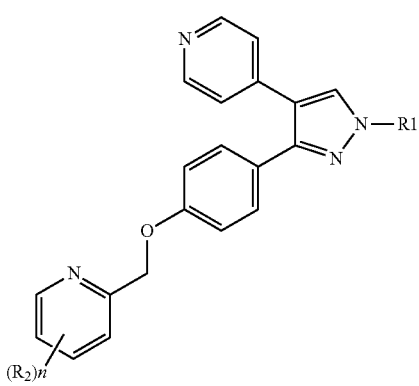

(I)

or a stereoisomeric form thereof, wherein
$R^1$ is 2-fluoroethyl, 2,2,2-trifluoroethyl or 3-fluoropropyl;
n is 1, 2 or 3;
each $R^2$ independently is $C_{1-3}$alkyl, cyclopropyl, $C_{1-3}$alkyloxy, $C_{1-3}$alkyloxy, halo, trifluoromethyl, trifluoromethoxy, difluoromethoxy, or cyano,
wherein at least one F is [$^{18}$F],
or a solvate or a salt form thereof.

The invention also relates to precursor compounds for the synthesis of the compounds of Formula (I) as previously defined, said compounds having the Formula (VI).

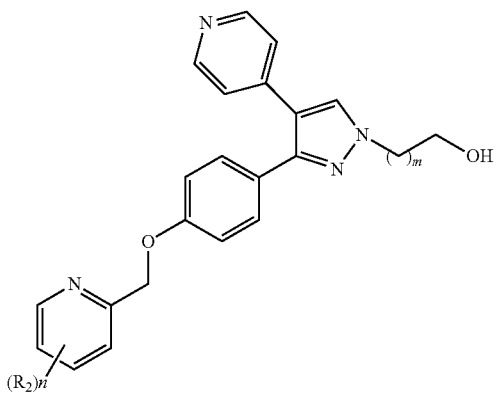

(VI)

or a stereoisomeric form thereof, wherein
m is 1 or 2;
n is 1, 2 or 3;
each $R^2$ independently is $C_{1-3}$alkyl, cyclopropyl, $C_{1-3}$alkyloxy, $C_{1-3}$alkyloxy, halo, trifluoromethyl, trifluoromethoxy, difluoromethoxy, or cyano,
or a solvate or a salt form thereof The invention also relates to reference compounds corresponding to the [$^{19}$F]-compounds of Formula (I).

Illustrative of the invention is a sterile composition comprising a compound of Formula (I) described herein, dissolved in an appropriate formulation.

Exemplifying the invention is a use of a compound of formula (I) as described herein, for, or a method of, imaging a tissue, cells or a host, in vitro or in vivo.

Further exemplifying the invention is a method of imaging a tissue, cells or a host, comprising contacting with or administering to a tissue, cells or a host a compound of Formula (I) as described herein, and imaging the tissue, cells or host with a positron-emission tomography imaging system.

Additionally, the invention refers to a process for the preparation of a compound according to Formula (I) as described herein, comprising the step of reacting a compound according to formula (V) as described herein, with $^{11}CH_3I$ or $^{11}CH_3OTf$ in the presence of a base in an inert solvent

DETAILED DESCRIPTION OF THE INVENTION

The present invention is directed to compounds of Formula (I) as defined hereinbefore and the pharmaceutically acceptable solvates and salt forms thereof. The present invention is further directed to precursor compounds of Formula (VI).

In one embodiment, $R^1$ is 2-fluoroethyl.

In another embodiment $R^2$ is 6-methyl, 3,5-dimethyl or 5-methoxy.

In a preferred embodiment, the compound of formula (I) is 2-[[4-[1-(2-fluoroethyl)-4-(4-pyridinyl)-1H-pyrazol-3-yl] phenoxy]methyl]-3,5-dimethyl-pyridine.succinate (B-3)

The compounds of Formula (I) and compositions comprising the compounds of Formula (I) can be used for imaging a tissue, cells or a host, in vitro or in vivo. In particular, the invention relates to a method of imaging or quantifying PDE10A in a tissue, cells or a host in vitro or in vivo.

The cells and tissues are preferably central nervous system cells and tissues in which PDE10A is abundant. As already mentioned, PDE10A is abundant in central nervous system tissue, more in particular, in central nervous system tissue forming the brain; more in particular, forming the striatum.

When the method is performed in vivo, the host is a mammal In such particular cases, the compound of Formula (I) is administered intravenously, for example, by injection with a syringe or by means of a peripheral intravenous line, such as a short catheter.

When the host is a human, the compound of Formula (I) or a sterile composition comprising a sterile saline solution of a compound of Formula (I), may in particular be administered by intravenous administration in the arm, into any identifiable vein, in particular in the back of the hand, or in the median cubital vein at the elbow.

Thus, in a particular embodiment, the invention relates to a method of imaging a tissue or cells in a mammal, comprising the intravenous administration of a compound of Formula (I), as defined herein, or a composition comprising a compound of Formula (I) to the mammal, and imaging the tissue or cells with a positron-emission tomography imaging system.

Thus, in a further particular embodiment, the invention relates to a method of imaging a tissue or cells in a human, comprising the intravenous administration of a compound of Formula (I), as defined herein, or a sterile saline composition comprising a compound of Formula (I) to the human, and imaging the tissue or cells with a positron-emission tomography imaging system.

In a further embodiment, the invention relates to a method of imaging or quantifying PDE10A in a mammal, comprising the intravenous administration of a compound of Formula (I), or a composition comprising a compound of Formula (I) to the mammal, and imaging with a positron-emission tomography imaging system.

In another embodiment, the invention relates to the use of a compound of Formula (I) for imaging a tissue, cells or a host, in vitro or in vivo, or the invention relates to a compound of Formula (I), for use in imaging a tissue, cells or a host in vitro or in vivo, using positron-emission tomography.

DEFINITIONS

"$C_{1-3}$alkyl", on its own or in combination with other terms shall denote a straight or branched saturated alkyl group having 1, 2 or 3 carbon atoms, e.g. methyl, ethyl, 1-propyl and 2-propyl.

As used herein, the term "composition" is intended to encompass a product comprising the specified ingredients in the specified amounts, as well as any product which results, directly or indirectly, from combinations of the specified ingredients in the specified amounts.

The term "stereoisomeric forms" as used hereinbefore or hereinafter, defines all the possible stereoisomeric forms which the addition salts of compounds according to formula (I) and their addition salts may possess. Unless otherwise mentioned or indicated, the chemical designation of compounds denotes the mixture of all possible stereochemically isomeric forms.

Acceptable salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of the present invention. The pharmaceutically acceptable salts are defined to comprise the therapeutically active non-toxic acid addition salt forms that the compounds according to Formula (I) are able to form. Said salts can be obtained by treating the base form of the compounds according to Formula (I) with appropriate acids, for example inorganic acids, for example hydrohalic acid, in particular hydrochloric acid, hydrobromic acid, sulphuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzensulfonic acid, p-toluenesulfonic acid, cyclamic acid, salicylic acid, p-aminosalicylic acid and pamoic acid.

Conversely, said salt forms can be converted into the free base form by treatment with an appropriate base.

The term "host" refers to a mammal, in particular to humans, rats, mice, dogs and rats.

The term "cell" refers to a cell expressing or incorporating the PDE10A enzyme.

The pyridine compounds of the present invention differ structurally from the prior art compounds which invariably comprise a heteroaromatic bicyclic moiety. Functionally they differ in that they have reduced lipophilicity and, therefore, they exhibit less non-specific binding to brain proteins and fat, making them more attractive as potential PET radioligands. When compared to 2-{4-[1-(2-[$^{18}$F]fluoroethyl)-4-pyridin-4-yl-1H-pyrazol-3-yl]-phenoxymethyl}-quinoline, the compounds of the present invention have faster kinetics resulting in shorter acquisition times in clinical application to obtain robust distribution volume values and reach higher striatum-to-cerebellum ratios resulting in higher quality in vivo images and more accurate quantification of the PDE10A binding potential.

Preparation

The compounds according to the invention can generally be prepared by a succession of steps, each of which is known to the skilled person. In particular, the compounds can be prepared according to the following synthesis methods.

A. Preparation of the Final Compounds

Compounds of Formula (I) in their non-radiolabelled version can be prepared by synthesis methods well known by the person skilled in the art. Compounds of the invention may be prepared, for example, by three different general methods:

Method A:

Following the reaction sequence shown in scheme 2.

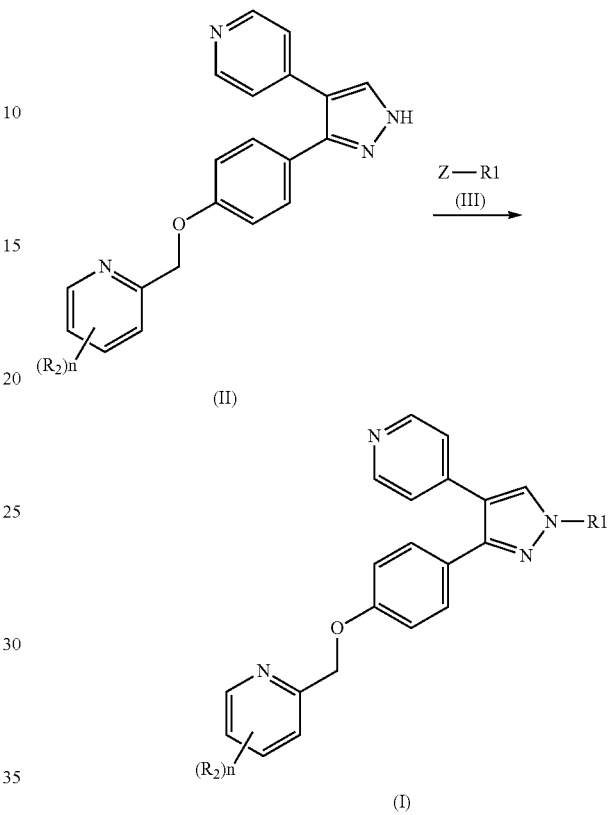

Thus, compound of Formula (II) may be reacted with a commercially available alkylating agent of Formula (III), wherein Z is a suitable leaving group such as halo, for example bromo or iodo, in the presence of a suitable base such as cesium carbonate or potassium carbonate, in an inert solvent such as, for example, dimethylformamide, stirring the reaction mixture at a suitable temperature, typically at 100-150° C., using conventional heating or under microwave irradiation, for the required time to achieve completion of the reaction, typically 10-20 minutes in a microwave oven. The alkylation reaction usually affords a mixture of the two possible regioisomers, derived from the alkylation on both nitrogen atoms of the pyrazole ring, which can be separated by chromatographic methods, either by column chromatography or HPLC. Alternatively, Z may be a hydroxyl group, in which case reaction with compound (II) can be performed using conventional Mitsunobu conditions, which are well known by the person skilled in the art. Thus, compound (II) can be reacted with compound (III) wherein Z is hydroxyl- in the presence of diethyl-, di-tert-butyl- or diisopropyl azodicarboxylate and triphenylphosphine, in an inert solvent such as for example tetrahydrofuran, stirring the reaction mixture at a suitable temperature, typically at 120° C. under microwave irradiation, for a suitable period of time to allow completion of the reaction, typically 20 minutes. The Mitsunobu reaction usually affords a mixture of the two possible regioisomers, derived from the alkylation on both nitrogen atoms of the pyrazole ring, which can be separated by chromatographic methods, either by column chromatography or HPLC.

Method B:

Alternatively, compounds of formula (I) can also be prepared by a reaction sequence as shown in scheme 3.

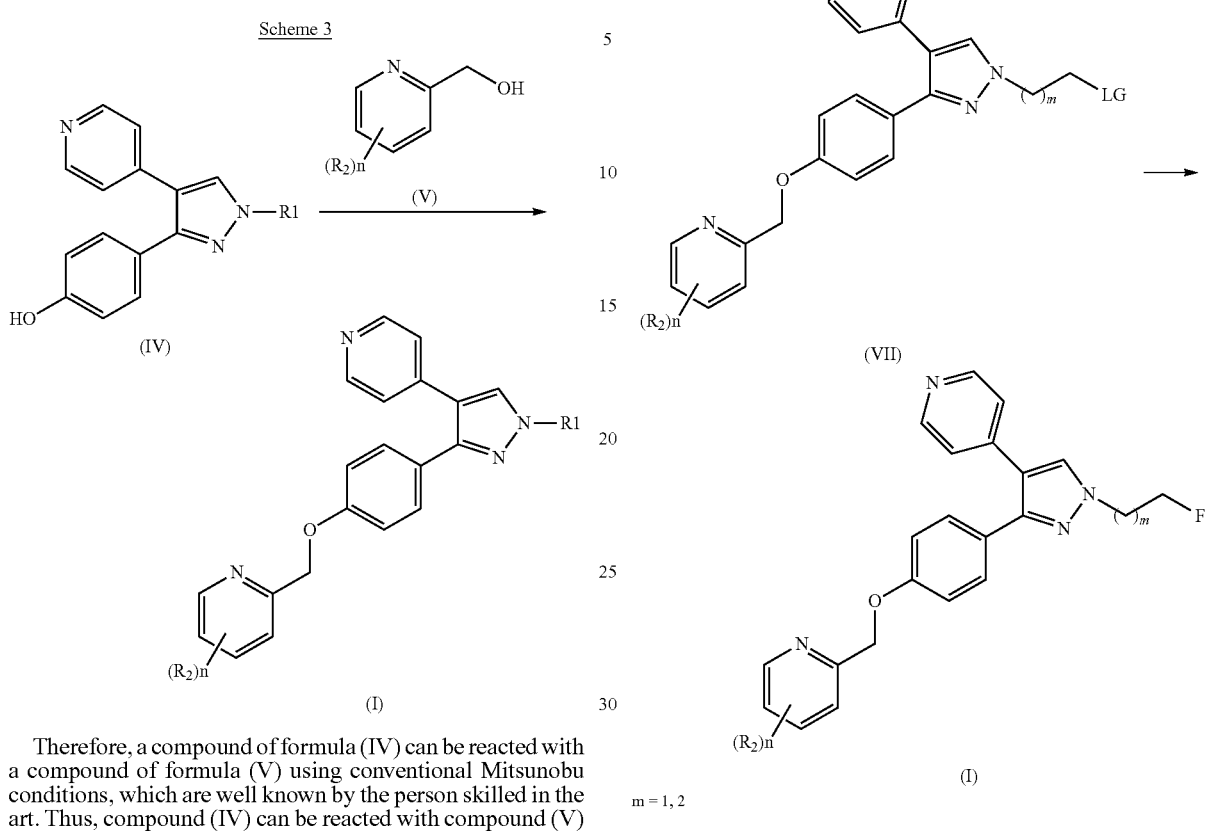

Therefore, a compound of formula (IV) can be reacted with a compound of formula (V) using conventional Mitsunobu conditions, which are well known by the person skilled in the art. Thus, compound (IV) can be reacted with compound (V) in the presence of diethyl-, di-tert-butyl- or diisopropyl azodicarboxylate and triphenylphosphine, in an inert solvent such as for example tetrahydrofuran, stirring the reaction mixture at a suitable temperature, typically at 120° C. under microwave irradiation, for a suitable period of time to allow completion of the reaction, typically 15-20 minutes. Compounds of formula (V) are either commercially available or are described in chemical literature and can be prepared by simple standard synthetic procedures well known by the skilled person.

Method C:

Alternatively, compounds of formula (I) wherein R1 is 2-fluoroethyl or 3-fluoropropyl, may also be prepared by a reaction sequence as shown in scheme 4.

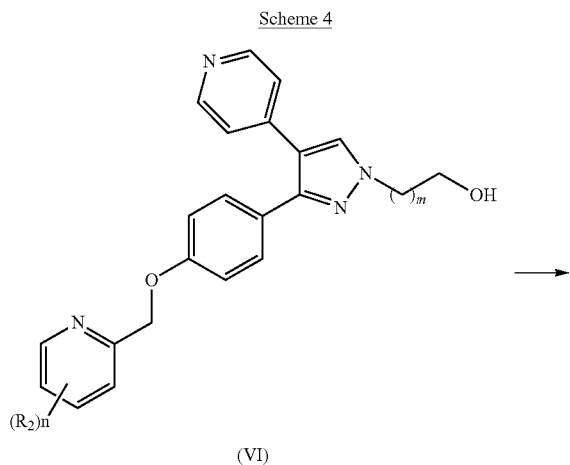

Therefore, in a compound of formula (VI) the hydroxyl group may be transformed into a suitable leaving group LG, such as methanesulfonate or tosylate, by methods well known by those skilled in the art, affording an intermediate of formula (VII). Then the leaving group can be replaced by fluorine using standard methods well known by the skilled person, such as, for example, reacting with tetrabutylammonium fluoride in an inert solvent such as for example tetrahydrofuran, stirring the reaction mixture at a suitable temperature, typically at 70° C. under microwave irradiation, for a suitable period of time to allow completion of the reaction, typically 10 minutes. Alternatively, compounds of formula (I) can also be prepared by direct reaction of an intermediate of formula (VI) with a fluorinating agent such as, for example, (N,N-diethylamino)sulphur trifluoride (DAST), by art known procedures.

The incorporation of radioactive fluorine atoms into the R1 side chain of compounds of formula (I) wherein R1 is 2-fluoroethyl or 3-fluoropropyl, may be performed using techniques known in the art, for example, by reaction of a suitable precursor of formula (VII) with a nucleophilic radioactive fluorinating reagent, such as K[$^{18}$F]/Kryptofix® 222 or tetraalkyl ammonium salts incorporating radioactive fluoride, in an inert solvent such as, for example, dimethylformamide, stirring the reaction mixture at a suitable temperature, using conventional heating or under microwave irradiation, for the required time to achieve completion of the reaction. Alternatively, the incorporation of radioactive fluorine can also be performed by the alkylation reaction of an intermediate of formula (II) with either 1-bromo-2-[$^{18}$F]fluoroethane or 1-bromo-3-[$^{18}$F]fluoropropane—in the presence of a base such as, for example, cesium carbonate, in an inert solvent such as, for example, dimethylformamide, stirring the reaction mixture at a suitable temperature, using conventional heating or under microwave irradiation, for the required time to achieve completion of the reaction, typically 15 minutes at 90° C. using conventional heating. In this case the desired radiolabelled compound (I) can be separated from the other radiolabelled regioisomer and from the unreacted precursor by HPLC.

The incorporation of either radioactive carbon atoms or radioactive fluorine atoms into the R2 substituent groups of compounds of formula (I) may also be performed using radiochemical techniques well known by those skilled in the art. For example, a [$^{11}$C]-methoxy group can be incorporated by reaction of a suitable precursor of formula (I), wherein one R2 is OH, with [$^{11}$C]CH$_3$I or [$^{11}$C]CH$_3$OTf in the presence of a base, such as for example cesium carbonate, in an inert solvent such as for example dimethylformamide, stirring the reaction mixture at a suitable temperature using conventional heating-, for a suitable period of time to allow completion of the reaction.

Incorporation of a radioactive fluorine atom in R2 can be achieved, for example, by reaction of a suitable precursor of formula (I) wherein one R2 is a nitro group, a chlorine or a bromine in either position 4 or 6 of the pyridinyl ring, with a nucleophilic radioactive fluorinating reagent, such as K[$^{18}$F]/Kryptofix® 222, in an inert solvent such as, for example, dimethylformamide, dimethylsulfoxide or acetonitrile, stirring the reaction mixture at a suitable temperature using conventional heating or under microwave irradiation, for the required time to achieve completion of the reaction.

The transformations of different functional groups present in the final compounds, into other functional groups according to Formula (I), can be performed by synthesis methods well known by the person skilled in the art. Thus, for instance, a compound of formula (I) wherein R2 is a bromine atom can react with (fluorosulfonyl)difluoroacetic acid methyl ester, in the presence of cuprous iodide in an inert solvent such as, for example, dimethylformamide, stirring the reaction mixture at a suitable temperature, typically at 120° C., using conventional heating or under microwave irradiation, for the required time to achieve completion of the reaction, typically 2 h of conventional heating, to yield a compound of formula (I) wherein R2 is trifluoromethyl. In another example, a compound of formula (I) wherein R2 is a bromine atom can be reacted with an alkyl- or cycloalkylboronic acid, in the presence of a suitable base such as, for example, aqueous sodium carbonate and a palladium complex catalyst such as, for example, palladium (0) tetrakis(triphenylphosphine) in an inert solvent such as, for example, dioxane, stirring the reaction mixture at a suitable temperature using conventional heating or under microwave irradiation, for the required time to achieve completion of the reaction, typically 15 minutes at 130° C. in a microwave oven, to yield a compound of formula (I) wherein R2 is C1-3alkyl or cyclopropyl.

B. Preparation of the Intermediate Compounds

Intermediate compounds of formula (II) can be prepared by synthesis methods well known by the person skilled in the art, such as, for example, by the reaction sequence shown in scheme 5, which is based on the method described in *J. Med. Chem.* 2009, 52 (16), 5188-5196.

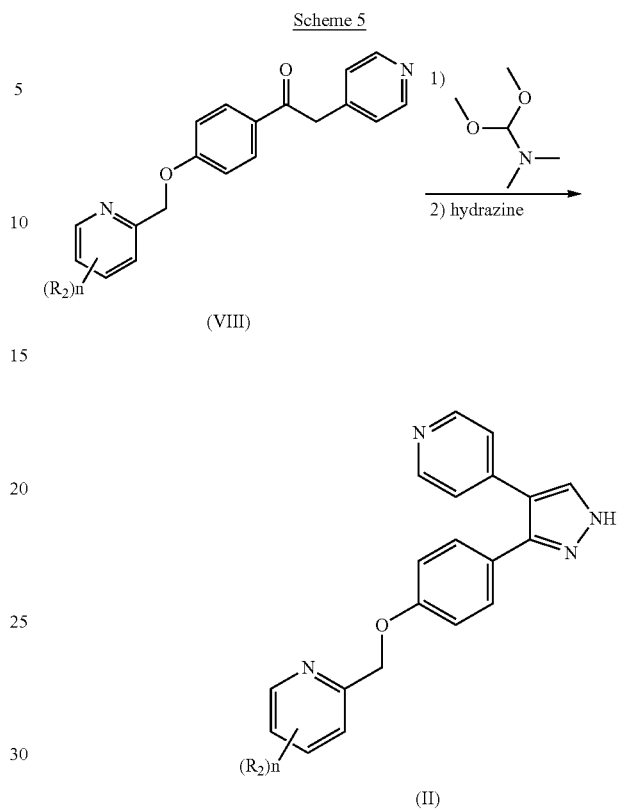

Therefore, a compound of Formula (VIII) may be reacted with excess commercially available dimethoxymethyl-dimethylamine, stirring the reaction mixture at reflux temperature for the required time to achieve completion of the reaction, typically 1 hour. After evaporation to dryness the resulting residue can be treated with hydrazine hydrate in methanol, stirring the reaction mixture at reflux temperature for the required time to achieve completion of the reaction, typically 1 hour.

Intermediate compounds of formula (VIII) can be prepared by a three steps sequence reaction, following essentially the same synthesis method as described in *J. Med. Chem.* 2009, 52 (16), 5188-5196, as it is shown in scheme 6.

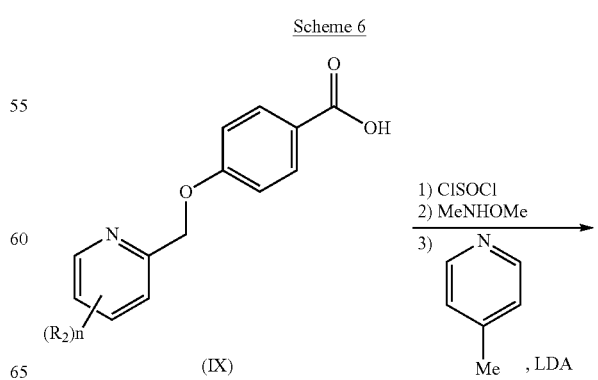

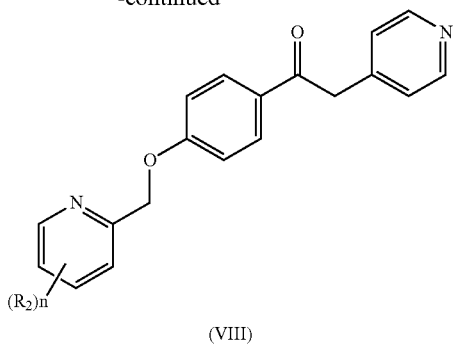

(VIII)

Therefore, a compound of formula (IX) can be reacted first with thionyl chloride, in order to form the corresponding acyl chloride, and then in situ with O,N-dimethyl hydroxylamine, in the presence of a suitable base such as, for example, triethylamine, in an inert solvent such as, for example, tetrahydrofuran, stirring the reaction mixture at room temperature for the required time to achieve completion of the reaction, typically between 6 and 18 hours. The N-methoxy-N-methyl-benzamide thus obtained can be subsequently reacted with 4-picoline, in the presence of an organolithium reagent, typically lithium diisopropylamide, in an inert and dry solvent such as, for example, tetrahydrofuran, stirring the reaction mixture at −78° C. for the required period of time to ensure completion of the reaction.

Intermediate compounds of formula (IX) can be prepared by synthesis methods well known by the person skilled in the art, such as, for example, by the reaction sequence shown in scheme 7.

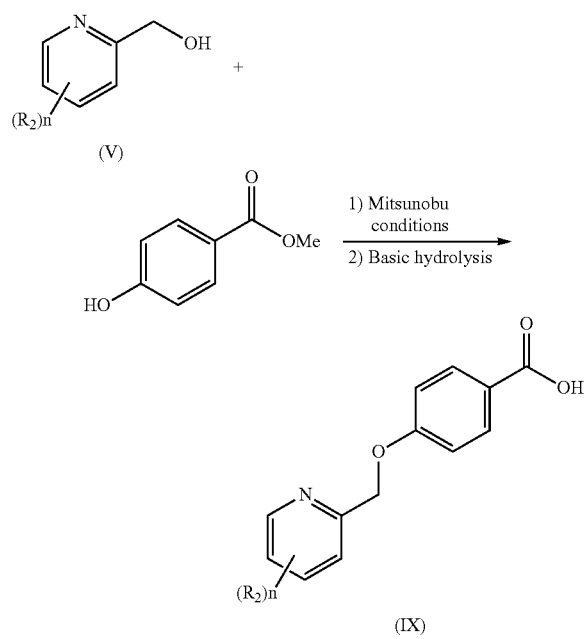

Therefore, a compound of formula (V) can be reacted first with commercially available 4-hydroxybenzoic acid methyl ester, using conventional Mitsunobu conditions, which are well known by the person skilled in the art. Thus, compound (V) can be reacted with 4-hydroxybenzoic acid methyl ester in the presence of diethyl-, di-tert-butyl- or diisopropyl azodicarboxylate and triphenylphosphine, in an inert solvent such as for example tetrahydrofuran, stirring the reaction mixture at a suitable temperature, typically at 120° C. under microwave irradiation, for a suitable period of time to allow completion of the reaction, typically 20 minutes. Subsequently, the corresponding methyl ester derivative of compound (IX) thus obtained may be hydrolized in basic conditions, using a diluted base such as, for example, aqueous sodium hydroxide or potassium hydroxide in an inert solvent such as, for example, methanol, tetrahydrofuran or a mixture methanol/tetrahydrofuran, stirring the reaction mixture at a suitable temperature, either at room temperature for a suitable period of time to allow completion of the reaction, typically 18 hours, or at 150° C. under microwave irradiation for 10 minutes. Compounds of formula (V) are either commercially available or are described in chemical literature and can be prepared by simple standard synthetic procedures well known by the skilled person.

Intermediate compounds of formula (IV) can be prepared by synthesis methods well known by the person skilled in the art, such as, for example, by the reaction sequence shown in scheme 8.

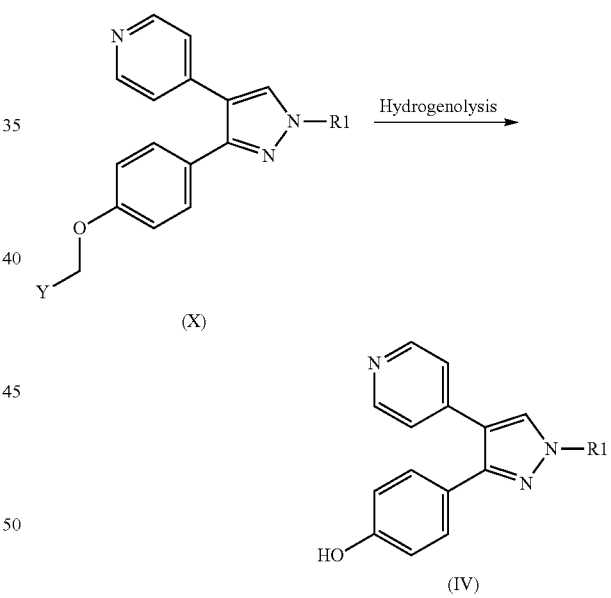

Therefore, a compound of formula (X) wherein Y is phenyl or 2-quinolinyl can be subjected to a hydrogenolysis reaction, in a suitable inert solvent such as, for example, ethanol, in the presence of a catalyst such as, for example, 5% or 10% palladium on activated carbon, for a period of time that ensures the completion of the reaction, typically at 50-80° C. and 1 atmosphere of hydrogen in an H-cube apparatus.

Intermediate compounds of formula (X) can be prepared by synthesis methods well known by the person skilled in the art, for example, in a similar fashion as previously defined in method A for the synthesis of compounds of formula (I), by the reaction sequence shown in scheme 9.

Scheme 9

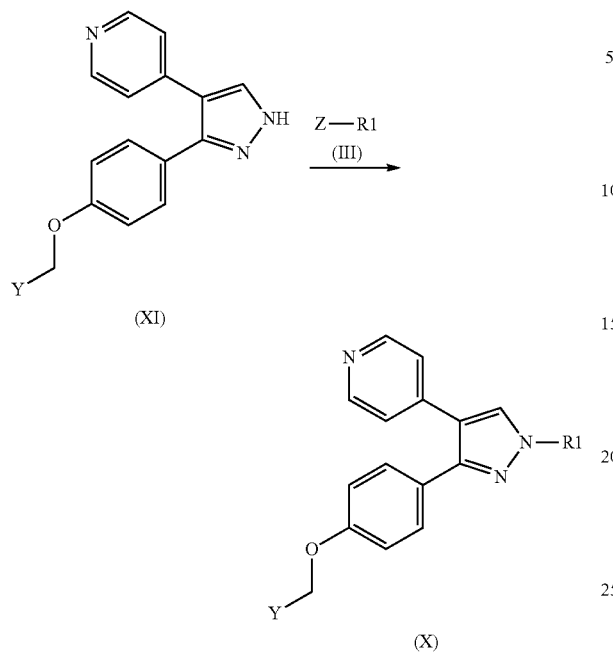

Thus, a compound of formula (XI) wherein Y is phenyl or 2-quinolinyl may be reacted with a commercially available alkylating agent of Formula (III), wherein Z is a suitable leaving group such as halo, for example bromo or iodo, in the presence of a suitable base such as cesium carbonate or potassium carbonate, in an inert solvent such as, for example, dimethylformamide, stirring the reaction mixture at a suitable temperature, typically at 100-150° C., using conventional heating or under microwave irradiation, for the required time to achieve completion of the reaction, typically 5-20 minutes in a microwave oven. In the particular case when R1 is —CH$_2$—CO-OAlk, the typical reaction temperature is room temperature and the required time is 3 hours. The alkylation reaction usually affords a mixture of the two possible regioisomers, derived from the alkylation on both nitrogen atoms of the pyrazole ring, which can be separated by chromatographic methods, either by column chromatography or HPLC. Alternatively, Z may be a hydroxyl group, in which case reaction with compound (XI) can be performed using conventional Mitsunobu conditions, which are well known by the person skilled in the art. Thus, compound (XI) can be reacted with compound (III) wherein Z is hydroxyl in the presence of diethyl-, di-tert-butyl- or diisopropyl azodicarboxylate and triphenylphosphine, in an inert solvent such as for example tetrahydrofuran, stirring the reaction mixture at a suitable temperature, typically at 120° C. under microwave irradiation, for a suitable period of time to allow completion of the reaction, typically 20 minutes. The Mitsunobu reaction usually affords a mixture of the two possible regioisomers, derived from the alkylation on both nitrogen atoms of the pyrazole ring, which can be separated by chromatographic methods, either by column chromatography or HPLC.

The synthesis of compound of formula (XI) wherein Y is phenyl is described in patent application WO2006/072828. The synthesis of compound of formula (XI) wherein Y is 2-quinolinyl is described in *J. Med. Chem.* 2009, 52 (16), 5188-5196.

Intermediate compounds of formula (VI) may be prepared by synthesis methods well known by the person skilled in the art, such as, for example, by the reaction sequence shown in scheme 10.

Scheme 10

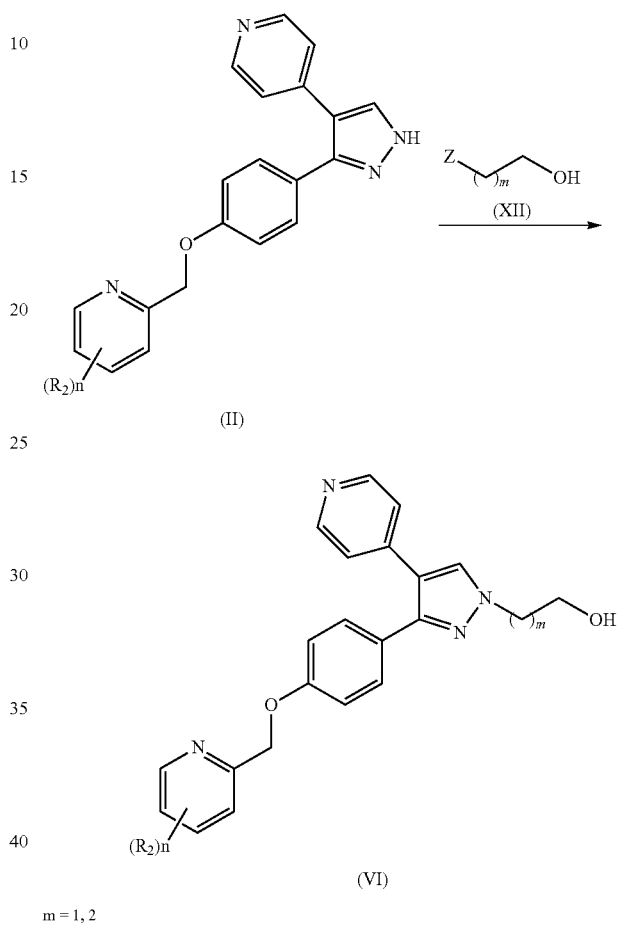

Therefore, a compound of Formula (II) may be reacted with a commercially available alkylating agent of Formula (XII), in which Z is a suitable leaving group such as halo, bromo being the most preferred, in the presence of a suitable base such as cesium carbonate or potassium carbonate, in an inert solvent such as, for example, dimethylformamide, stirring the reaction mixture at a suitable temperature, typically at 100° C., using conventional heating or under microwave irradiation, for the required time to achieve completion of the reaction, typically 10 minutes in a microwave oven. The alkylation reaction usually affords a mixture of the two possible regioisomers, derived from the alkylation on both nitrogen atoms of the pyrazole ring, which can be separated by chromatographic methods, either by column chromatography or HPLC.

Alternatively, compounds of formula (VI-a) wherein n is 1 can also be prepared by the sequence of reactions shown in scheme 11.

Scheme 11

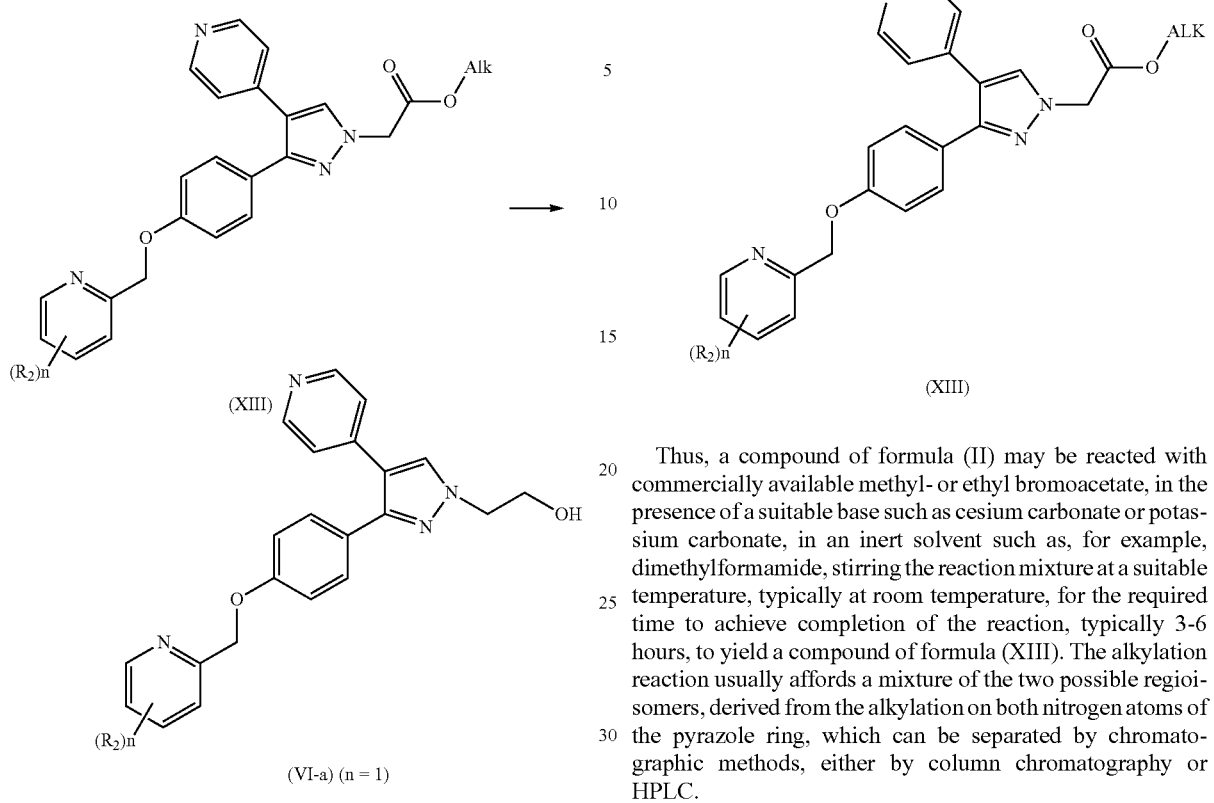

Thus, the ester group of a compound of formula (XIII) can be reduced to alcohol by synthesis methods well known by the person skilled in the art, such as, for example, reaction with sodium borohydride or sodium cyanoborohydride, in a suitable inert solvent or mixture of solvents, such as for example dichloromethane and methanol, stirring the reaction mixture at a suitable temperature, typically at room temperature, for the required time to achieve completion of the reaction, typically 2 hours, to afford the compound of formula (VI-a) wherein n is 1.

Intermediate compounds of formula (XIII) can be prepared by synthesis methods well known by the person skilled in the art, such as, for example, by the reaction sequence shown in scheme 12.

Scheme 12

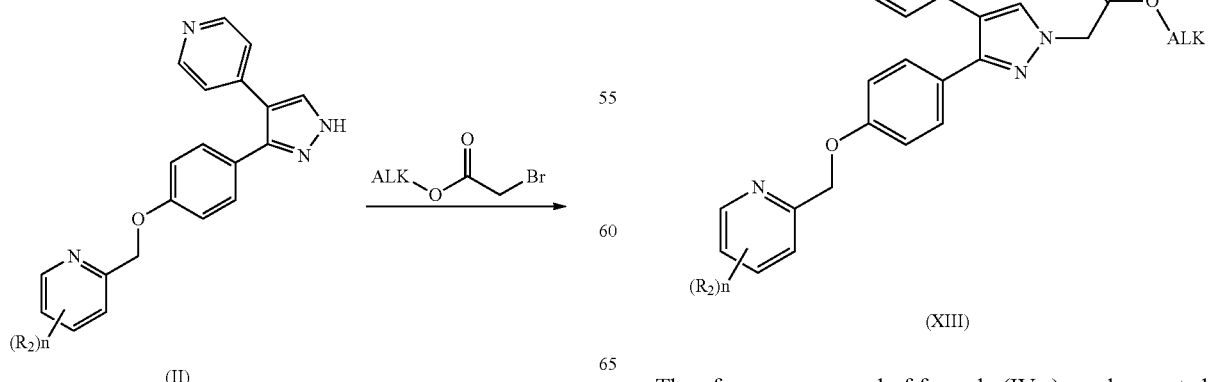

Thus, a compound of formula (II) may be reacted with commercially available methyl- or ethyl bromoacetate, in the presence of a suitable base such as cesium carbonate or potassium carbonate, in an inert solvent such as, for example, dimethylformamide, stirring the reaction mixture at a suitable temperature, typically at room temperature, for the required time to achieve completion of the reaction, typically 3-6 hours, to yield a compound of formula (XIII). The alkylation reaction usually affords a mixture of the two possible regioisomers, derived from the alkylation on both nitrogen atoms of the pyrazole ring, which can be separated by chromatographic methods, either by column chromatography or HPLC.

Alternatively, an intermediate compound of formula (XIII) can also be prepared by a reaction sequence as shown in scheme 13.

Scheme 13

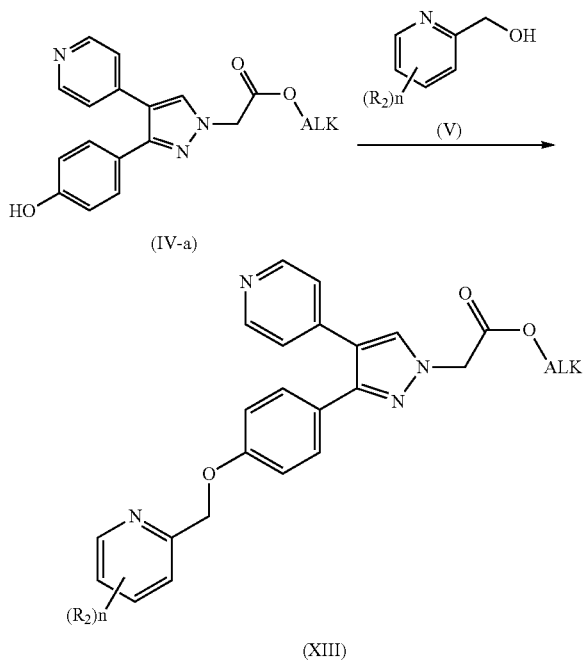

Therefore, a compound of formula (IV-a) can be reacted with a compound of formula (V) using conventional Mitsunobu conditions, which are well known by the person skilled in the art. Thus, compound (IV-a) can be reacted with compound (V) in the presence of diethyl-, di-tert-butyl- or diisopropyl azodicarboxylate and triphenylphosphine, in an inert solvent such as for example tetrahydrofuran, stirring the reaction mixture at a suitable temperature, typically at 120° C. under microwave irradiation, for a suitable period of time to allow completion of the reaction, typically 15-20 minutes. The compound of formula (IV-a) can be synthesized following the hydrogenolysis reaction sequence that is shown above in scheme 8, starting from a compound of formula (X-a) wherein R1 is —CH2-CO—OAlk, which can be synthesized according to the reaction sequence shown above in scheme 9.

The activity of compounds of Formula (I) was determined by measuring rat PDE10A2-cAMP inhibition and the pIC50 ranged from 6.60 to 8.79. The selectivity over other PDEs was also measured and it was in all cases >50 fold and in most of the compounds >100 fold.

Applications

The compounds according to the present invention find various applications for imaging tissues, cells or a host, both in vitro and in vivo. Thus, for instance, they can be used to map the differential distribution of PDE10 in subjects of different age and sex. Further, they allow one to explore for differential distribution of PDE10 in subjects afflicted by different diseases or disorders. Thus, abnormal distribution may be helpful in diagnosis, case finding, stratification of subject populations, and in monitoring disease progression in individual subjects. The radioligands may further find utility in determining PDE10A site occupancy by other ligands. As the radioligands are administered in trace amounts, no therapeutic effect will result therefrom.

Experimental Part
I. Chemistry:

Hereinafter, the term "LCMS" means liquid chromatography/mass spectrometry, "GCMS" means gas chromatography/mass spectrometry, "HPLC" means high-performance liquid chromatography, "DCM" means dichloromethane, "DMF" means dimethylformamide, "EtOAc" means ethyl acetate, "THF" means tetrahydrofuran, "min." means minutes, "h." means hours, "$R_t$" means retention time (in minutes), "[M+H]$^+$" means the protonated mass of the free base of the compound, "[M−H]$^-$" means the deprotonated mass of the free base of the compound, 'm.p." means melting point.

Microwave assisted reactions were performed in a single-mode reactor: Biotage Initiator™ Sixty microwave reactor (Biotage) or in a multimode reactor: MicroSYNTH Labstation (Milestone, Inc.).

Hydrogenation reactions were performed in a continuous flow hydrogenator H-CUBE® from ThalesNano Nanotechnology Inc.

Thin layer chromatography (TLC) was carried out on silica gel 60 F254 plates (Merck) using reagent grade solvents. Flash column chromatography was performed on silica gel, mesh 230-400 particle size and 60 A pore size (Merck) under standard techniques. Automated flash column chromatography was performed using ready-to-connect cartridges from Merck, on irregular silica gel, particle size 15-40 µm (normal phase disposable flash columns) on an SPOT or FLASH system from Armen Instrument.

Several methods for preparing the compounds of this invention are illustrated in the following examples, which are intended to illustrate but not to limit the scope of the present invention. Unless otherwise noted, all starting materials were obtained from commercial suppliers and used without further purification.

A. Synthesis of Intermediates and Precursors

Intermediate 1

4-(6-Methyl-pyridin-2-ylmethoxy)-benzoic acid methyl ester (I-1)

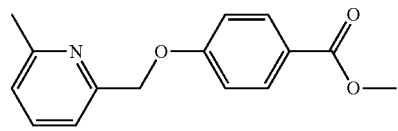 [SMILES: COC(=O)c1ccc(OCc2cccc(C)n2)cc1]

A mixture of 6-methyl-2-pyridinemethanol (7.0 g, 56.84 mmol), methyl 4-hydroxybenzoate (8.65 g, 56.84 mmol), diisopropyl azodicarboxylate (14.65 mL, 73.9 mmol) and triphenylphosphine (19.38 g, 73.9 mmol) in THF (42 mL) was heated in a microwave oven at 120° C. for 20 min (the reaction was divided in 7 batches). After this time the mixture was quenched with water, extracted with DCM, the solvent was evaporated to dryness in vacuo and the crude residue was purified by column chromatography (silicagel; heptane/EtOAc from 80/20 to 50/50). The desired fractions were collected and evaporated in vacuo to yield the desired intermediate I-1 as an orange oil around 50% pure, the main impurity being triphenylphosphine oxide. The mixture was used in the next reaction step without further purification (25 g, 85.5%). $C_{15}H_{15}NO_3$.

Intermediate 2

4-(6-Methyl-pyridin-2-ylmethoxy)-benzoic acid (I-2)

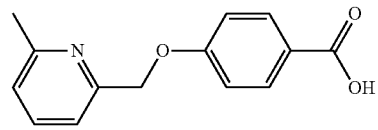

To a solution of intermediate I-1 in 150 mL of a mixture of methanol/THF (2:1) was added 2 M aqueous sodium hydroxide (49 mL, 97.2 mmol). The reaction mixture was stirred at room temperature overnight, then at 60° C. for 2 h. After evaporation of the organic solvent the aqueous phase was washed with EtOAc and then acidified with diluted HCl to pH is 5-6. Intermediate compound 1-2 that precipitated was filtered off, dried and used for the next reaction step without further purification (9.0 g, 76.2%). $C_{14}H_{13}NO_3$.

Intermediate 3

N-Methoxy-N-methyl-4-(6-methyl-pyridin-2-yl-methoxy)-benzamide (I-3)

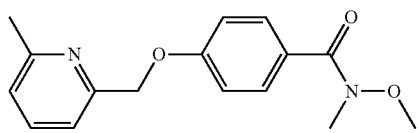

A mixture of intermediate 1-2 (9.0 g, 37.0 mmol) and thionyl chloride (50 mL) was stirred at room temperature for 3 h. The mixture was then concentrated to dryness and the crude acid chloride was dissolved in THF (100 mL). Then triethylamine (20.5 mL, 148 mmol) and O,N-dimethyl-hydroxylamine hydrochloride (10.8 g, 111 mmol) were slowly added. The reaction mixture was stirred at room temperature overnight. After quenching with water, the mixture was extracted with EtOAc, dried over sodium sulphate, filtered and evaporated in vacuo. The residue was purified by column chromatography (silicagel; heptane/EtOAc from 40/60 to 0/100) to give intermediate compound 1-3 as an orange oil that was used for the next reaction without further purification (6.2 g, 46.8%). $C_{16}H_{18}N_2O_3$.

Intermediate 4

2-Pyridin-4-yl-1-[4-(6-methyl-pyridin-2-ylmethoxy)-phenyl]-ethanone (I-4)

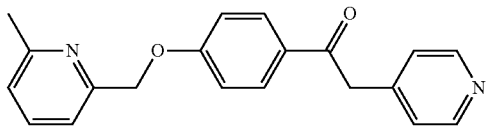

To a solution of lithium diisopropylamide (2 M solution in THF, 43.3 mL, 86.6 mmol) in THF (35 mL) was added dropwise 4-methylpyridine (8.43 mL, 86.6 mmol) at 0° C. under nitrogen. After 30 min it was cooled down to −78° C. and 35 mL of this solution was added dropwise to another solution of intermediate 1-3 (6.2 g, 17.32 mmol) in THF (65 mL) also cooled to −78° C. The mixture was stirred at this temperature for 2 h and then 20 mL more of the initially prepared solution were added dropwise. The resulting solution was stirred at −78° C. for an additional hour. After this time the reaction mixture was quenched with water and extracted with DCM. The organic layer was dried over sodium sulphate, filtered and evaporated in vacuo. The crude residue obtained was washed and triturated with diethyl ether affording intermediate compound 1-4 (4.7 g, 85.2%) as a pale yellow solid. $C_{20}H_{18}N_2O_2$.

Intermediate 5

2-Methyl-6-[4-(4-pyridin-4-yl-2H-pyrazol-3-yl)-phenoxymethyl]-pyridine (I-5)

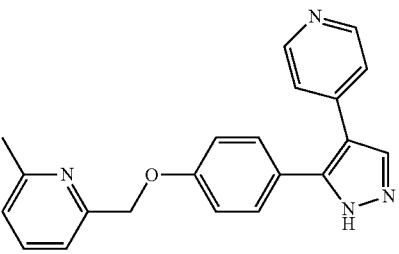 [SMILES: Cc1cccc(COc2ccc(-c3[nH]ncc3-c3ccncc3)cc2)n1]

A solution of intermediate I-4 (4.7 g, 14.76 mmol) in dimethoxymethyl-dimethylamine (15 mL) was stirred at reflux for 1 h. After evaporation of the solvent the crude residue was dissolved in methanol (50 mL) and hydrazine hydrate (1.08 mL, 22.14 mmol) was added. The reaction mixture was heated at reflux for 1 h, after which time the solvent was evaporated affording a solid residue that was washed and triturated with a mixture of diethyl ether/EtOAc, to yield intermediate compound 1-5 (3.4 g, 67.3%) as a pale yellow solid. $C_{21}H_{18}N_4O$. LCMS: Rt 2.48, m/z 343 $[M+H]^+$ (method 7).

Intermediate 6

4-[3-(4-Benzyloxy-phenyl)-1-(2-fluoroethyl)-1H-pyrazol-4-yl]-pyridine (I-6)

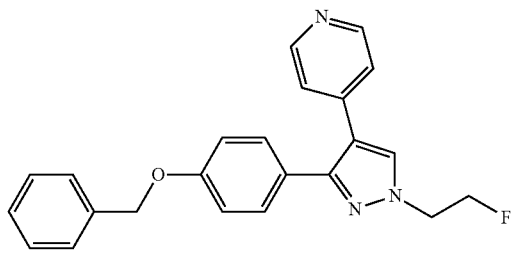 [SMILES: FCCn1cc(-c2ccncc2)c(-c2ccc(OCc3ccccc3)cc2)n1]

A mixture of 4-[3-(4-benzyloxy-phenyl)-1H-pyrazol-4-yl]-pyridine (6.7 g, 20.47 mmol) that was synthesized following the method described in patent application WO2006/072828, 1-bromo-2-fluoroethane (3.12 g, 24.56 mmol) and cesium carbonate (20 g, 61.4 mmol) in DMF (42 mL) was heated in a microwave oven at 150° C. for 5 min (the reaction was divided in 6 batches). After cooling to room temperature, the solid was discarded by filtration and the solution was quenched with water and further extracted with EtOAc. The organic phase was dried over sodium sulphate, filtered and evaporated in vacuo. The crude residue was purified by column chromatography (silicagel; acetonitrile/diisopropylether from 30/70 to 80/20, and then again with EtOAc/heptane 70/30). The desired fractions were collected and evaporated to dryness yielding the desired intermediate compound 1-6 (4 g, 52.3%) as an oil. $C_{23}H_{20}FN_3O$. LCMS: Rt 4.22, m/z 374 $[M+H]^+$ (method 1).

The corresponding regioisomer I-6' 4-[5-(4-benzyloxy-phenyl)-1-(2-fluoroethyl)-1H-pyrazol-4-yl]-pyridine was also isolated from the chromatographic purification (2 g, 26.2%). $C_{23}H_{20}FN_3O$.

Intermediate 7

4-[1-(2-Fluoroethyl)-4-pyridin-4-yl-1H-pyrazol-3-yl]-phenol (I-7)

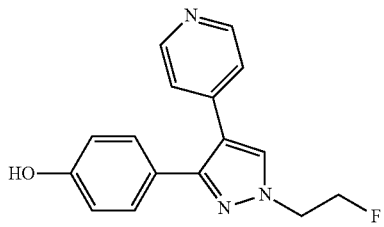 [SMILES: Oc1ccc(-c2nn(CCF)cc2-c2ccncc2)cc1]

Intermediate compound 1-6 (4 g, 10.71 mmol) was dissolved in ethanol (200 mL) and subjected to hydrogenation in a H-Cube® system using Pd/C 5% as catalyst (full hydrogen mode, 2.5 mL/min) at 80° C. and atmospheric pressure. The solvent was evaporated to dryness in vacuo affording intermediate compound 1-7 (2.5 g, 82.4%) that was used for the next reaction without further purification. $C_{16}H_{14}FN_3O$. LCMS: Rt 1.57, m/z 284 [M+H]$^+$ (method 8).

Intermediate 8

4-[1-(3-Fluoropropyl)-4-pyridin-4-yl-1H-pyrazol-3-yl]-phenol (I-8)

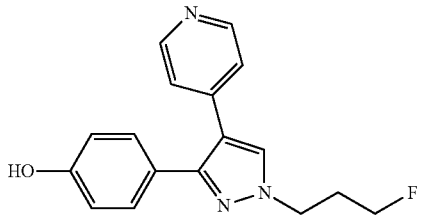 [SMILES: Oc1ccc(-c2nn(CCCF)cc2-c2ccncc2)cc1]

Following the procedure for the preparation of intermediate compound 1-7 but substituting 4-[3-(4-Benzyloxy-phenyl)-1-(2-fluoroethyl)-1H-pyrazol-4-yl]-pyridine for 4-[3-(4-Benzyloxy-phenyl)-1-(2-fluoropropyl)-1H-pyrazol-4-yl]-pyridine provided intermediate compound 1-8 (90%). $C_{17}H_{16}FN_3O$. LCMS: Rt 1.81, m/z 298 [M+H]$^+$ (method 7).

Intermediate 9

4-[3-(4-Benzyloxy-phenyl)-1-(2,2,2-trifluoroethyl)-1H-pyrazol-4-yl]-pyridine (I-9)

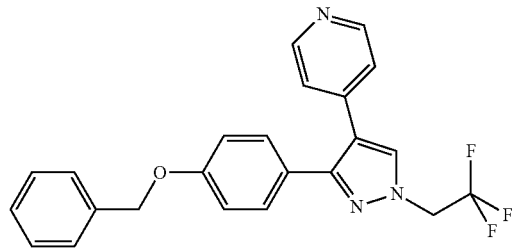 [SMILES: FC(F)(F)Cn1cc(-c2ccncc2)c(-c2ccc(OCc3ccccc3)cc2)n1]

A mixture of 4-[3-(4-benzyloxy-phenyl)-1H-pyrazol-4-yl]-pyridine (2.0 g, 6.11 mmol) that was synthesized following the method described in patent application WO2006/072828, 1,1,1-trifluoro-2-iodoethane (0.733 mL, 7.33 mmol) and cesium carbonate (5.97 g, 18.3 mmol) in DMF (12 mL) was heated in a microwave oven at 120° C. for 20 min. After cooling to room temperature the mixture was quenched with water and further extracted with EtOAc. The organic phase was dried over sodium sulphate, filtered and evaporated in vacuo. The crude residue was purified by column chromatography (silicagel; acetonitrile/diisopropylether from 50/50 to 80/20). The desired fractions were collected and evaporated to dryness yielding the desired intermediate compound 1-9 around 80% pure (1.2 g, 38.4%) as an oil. $C_{23}H_{18}F_3N_3O$. LCMS: Rt 4.86, m/z 410 [M+H]$^+$ (method 2).

The corresponding regioisomer I-9' 4-[5-(4-benzyloxy-phenyl)-1-(2,2,2-trifluoroethyl)-1H-pyrazol-4-yl]-pyridine was also isolated from the chromatographic purification (0.4 g, 14.6%). $C_{23}H_{18}F_3N_3O$.

Intermediate 10

4-[4-Pyridin-4-yl-1-(2,2,2-trifluoroethyl)-1H-pyrazol-3-yl]-phenol (I-10)

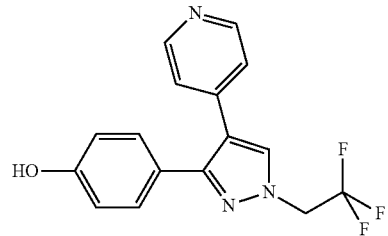 [SMILES: Oc1ccc(-c2nn(CC(F)(F)F)cc2-c2ccncc2)cc1]

Intermediate compound 1-9 was dissolved in ethanol (50 mL) and subjected to hydrogenation in a H-Cube® system using Pd/C 5% as catalyst (full hydrogen mode, 1.5 mL/min) at 80° C. and atmospheric pressure. The solvent was evaporated to dryness in vacuo affording intermediate compound I-10 (0.55 g, 75.4%) as a white solid, which was used for the next reaction without further purification. $C_{16}H_{12}F_3N_3O$. LCMS: Rt 1.82, m/z 320 [M+H]$^+$ (method 7).

Intermediate 11

{3-[4-(6-Methylpyridin-2-ylmethoxy)-phenyl]-4-pyridin-4-yl-pyrazol-1-yl}-acetic acid methyl ester (I-11) and {5-[4-(6-methylpyridin-2-ylmethoxy)-phenyl]-4-pyridin-4-yl-pyrazol-1-yl}-acetic acid methyl ester (I-11')

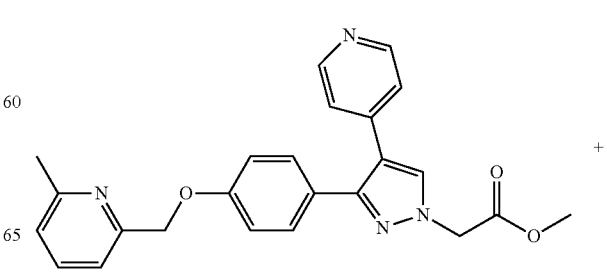

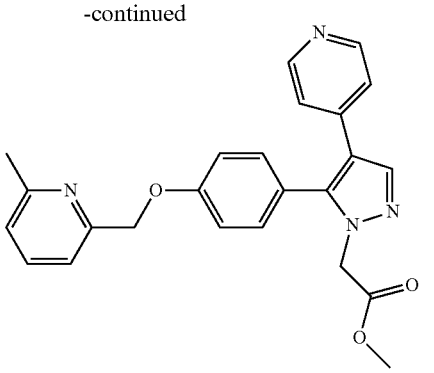

To a stirred solution of intermediate 1-5 (0.30 g, 0.876 mmol) in DMF (6 mL) were added methyl bromoacetate (0.10 mL, 1.051 mmol) and cesium carbonate (0.86 g, 2.63 mmol). The mixture was stirred at room temperature for 6 h. Then it was quenched with water and extracted with EtOAc. The organic solvents were separated, dried over sodium sulphate and evaporated to dryness in vacuo. The crude residue was purified by column chromatography (silicagel; EtOAc/methanol 100/0 to 90/10). The desired fractions were collected and evaporated in vacuo to yield a mixture of the two regioisomers I-11 and I-11' that was used as such for the next reaction without further purification (0.21 g, 49.2%). $C_{24}H_{22}N_4O_3$.

Intermediate 12

2-{3-[4-(6-Methylpyridin-2-ylmethoxy)-phenyl]-4-pyridin-4-yl-pyrazol-1-yl}-ethanol (I-12)

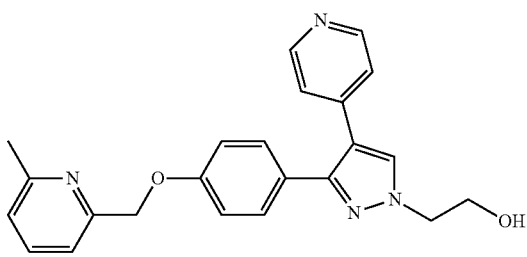 [SMILES: Cc1cccc(COc2ccc(-c3nn(CCO)cc3-c3ccncc3)cc2)n1]

To a stirred solution of the mixture of intermediates I-11 and I-11' (0.21 g, 0.507 mmol) in a mixture of DCM (4 mL) and methanol (1 mL) was added sodium borohydride (0.096 g, 2.536 mmol). The reaction mixture was stirred at room temperature for 3 h. The mixture was then quenched with water, extracted with more DCM, the organic solvent was dried over sodium sulphate and evaporated to dryness. The crude residue was purified by column chromatography (silicagel; EtOAc/methanol 100/0 to 90/10). The desired fractions were collected and evaporated in vacuo to yield intermediate compound I-12 (0.12 g, 61.2%). $C_{23}H_{22}N_4O_2$. LCMS: Rt 3.48, m/z 387 [M+H]$^+$ (method 3).

The corresponding regioisomer I-12' 2-{5-[4-(6-methylpyridin-2-ylmethoxy)-phenyl]-4-pyridin-4-yl-pyrazol-1-yl}-ethanol was also isolated from the chromatographic separation (0.045 g, 23%). $C_{23}H_{22}N_4O_2$.

Intermediate 13

{4-Pyridin-4-yl-3-[4-(quinolin-2-ylmethoxy)-phenyl]-pyrazol-1-yl}-acetic acid methyl ester (I-13) and {4-Pyridin-4-yl-5-[4-(quinolin-2-ylmethoxy)-phenyl]-pyrazol-1-yl}-acetic acid methyl ester (I-13')

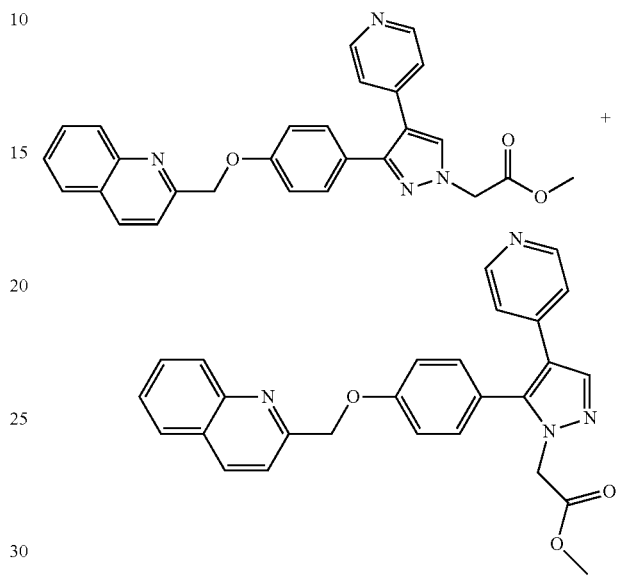

To a stirred solution of 2-[4-(4-Pyridin-4-yl-2H-pyrazol-3-yl)-phenoxymethyl]-quinoline (0.5 g, 1.33 mmol) which was synthesized following the method described in *J. Med. Chem.* 2009, 52 (16), 5188-5196, in DMF (10 mL) were added methyl bromoacetate (0.15 mL, 1.60 mmol) and cesium carbonate (1.30 g, 3.99 mmol). The mixture was stirred at room temperature for 3 h. Then it was quenched with water and extracted with EtOAc. The organic solvents were separated, dried over sodium sulphate and evaporated to dryness in vacuo. The crude residue was purified by column chromatography (silicagel; EtOAc/methanol 100/0 to 95/5). The desired fractions were collected and evaporated in vacuo to yield a mixture of the two regioisomers I-13 and I-13' that was used for the next reaction without further purification (0.47 g, 47%). $C_{27}H_{22}N_4O_3$.

Intermediate 14

[3-(4-Hydroxyphenyl)-4-pyridin-4-yl-pyrazol-1-yl] acetic acid methyl ester (I-14) and [5-(4-hydroxyphenyl)-4-pyridin-4-yl-pyrazol-1-yl]acetic acid methyl ester (I-14')

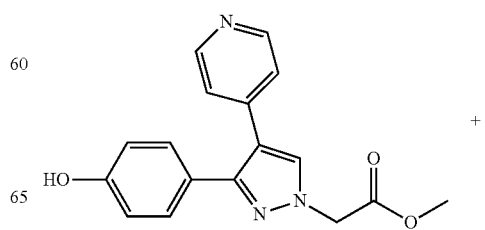

-continued

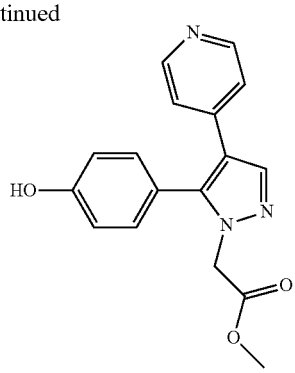

The mixture of intermediate compounds I-13 and 1-13' (0.47 g, 1.043 mmol) was dissolved in ethanol (20 mL) and subjected to hydrogenation in a H-Cube® system using Pd/C 5% as catalyst (full hydrogen mode, 1.5 mL/min) at 70° C. and atmospheric pressure. The solvent was evaporated to dryness in vacuo to give a yellow oil that was made solid by treatment with DCM. The solid was washed with more DCM yielding a mixture of the two intermediates I-14 and 1-14' that was used for the next reaction without further purification (0.235 g, 73%). $C_{17}H_{15}N_3O_3$. LCMS: Rt 0.95 (major regioisomer), Rt 1.00 (minor regioisomer), m/z 310 [M+H]$^+$ (method 8).

Intermediate 15

{3-[4-(3,5-Dimethylpyridin-2-ylmethoxy)-phenyl]-4-pyridin-4-yl-pyrazol-1-yl}-acetic acid methyl ester (I-15) and {5-[4-(3,5-dimethylpyridin-2-ylmethoxy)-phenyl]-4-pyridin-4-yl-pyrazol-1-yl}-acetic acid methyl ester (I-15')

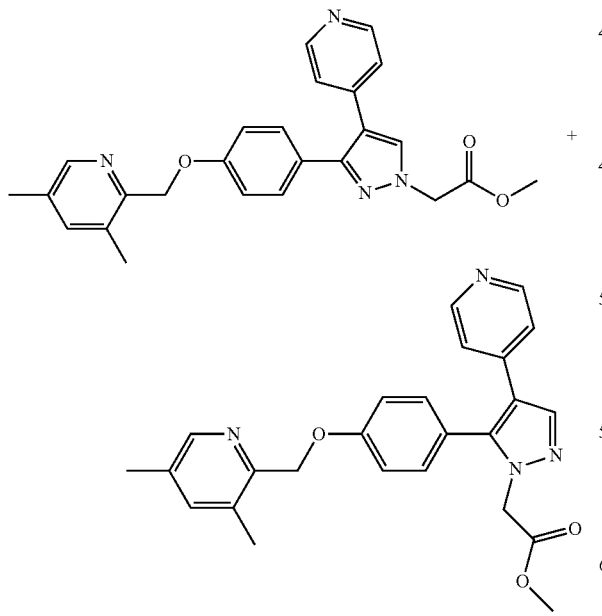

A mixture of the two regioisomers I-14 and I-14' (0.235 g, 0.760 mmol), 3,5-dimethyl-2-hydroxymethylpyridine (0.156 g, 1.14 mmol), diisopropyl azodicarboxylate (0.262 g, 1.14 mmol) and triphenylphosphine (0.299 g, 1.14 mmol) in THF (6 mL) was heated in a microwave oven at 120° C. for 20 min. After this time the mixture was quenched with a saturated aqueous solution of sodium carbonate, extracted with EtOAc, dried over sodium sulphate and the solvent was evaporated to dryness in vacuo. The crude residue was purified by column chromatography (silicagel; EtOAc/methanol 100/0 to 95/5). The desired fractions were collected and the solvent was evaporated in vacuo to yield a mixture of the two intermediate compounds I-15 and I-15' that was used for the next reaction without further purification (0.18 g, 55%). $C_{25}H_{24}N_4O_3$.

Intermediate 16

2-{3-[4-(3,5-Dimethylpyridin-2-ylmethoxy)-phenyl]-4-pyridin-4-yl-pyrazol-1-yl}-ethanol (I-16)

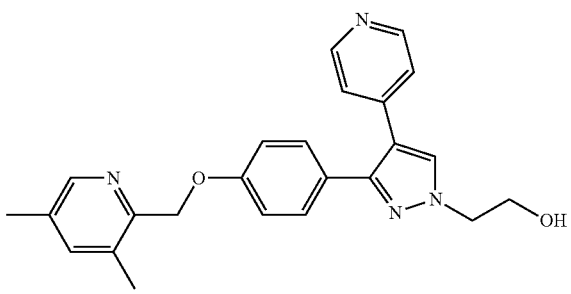 [SMILES: Cc1cnc(COc2ccc(-c3nn(CCO)cc3-c3ccncc3)cc2)c(C)c1]

To a stirred solution of the mixture of intermediates I-15 and I-15' (0.18 g, 0.420 mmol) in a mixture of DCM (4 mL) and methanol (1 mL) was added sodium borohydride (0.079 g, 2.10 mmol). The reaction mixture was stirred at room temperature for 1 h. The mixture was then quenched with water, extracted with more DCM, the organic solvent was dried over sodium sulphate and evaporated to dryness. The crude residue was purified by column chromatography (silicagel; EtOAc/methanol 100/0 to 90/10). The desired fractions were collected and evaporated in vacuo to yield intermediate compound 1-16 (0.12 g, 61.2%). The other regioisomer was not isolated from the chromatographic separation. $C_{24}H_{24}N_4O_2$. LCMS: Rt 2.53, m/z 401 [M+H]$^+$ (method 6).

Intermediate 17

{3-[4-(5-Methoxypyridin-2-ylmethoxy)-phenyl]-4-pyridin-4-yl-pyrazol-1-yl}-acetic acid methyl ester (I-17) and {5-[4-(5-methoxypyridin-2-ylmethoxy)-phenyl]-4-pyridin-4-yl-pyrazol-1-yl}-acetic acid methyl ester (I-17')

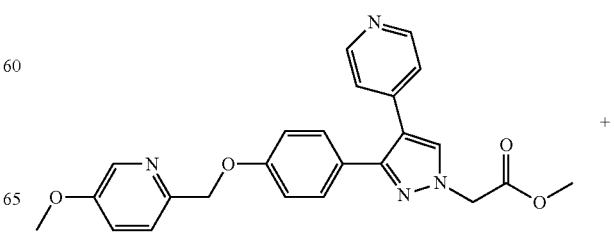

-continued

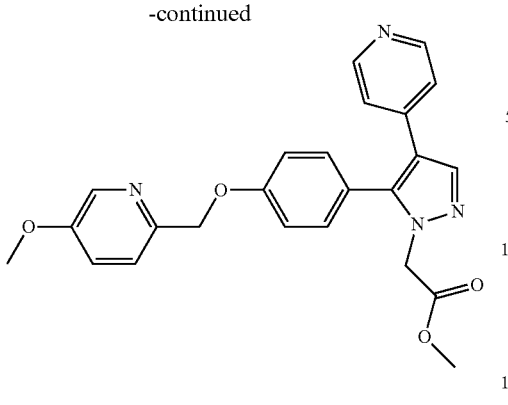

A mixture of the two regioisomers I-14 and I-14' (0.17 g, 0.550 mmol), (5-methoxy-pyridin-2-yl) methanol (0.115 g, 0.825 mmol) as described in Bioorg. Med. Chem. 2005, 13, 6763-6770, diisopropyl azodicarboxylate (0.190 g, 0.825 mmol) and triphenylphosphine (0.216 g, 0.825 mmol) in THF (4 mL) was heated in a microwave oven at 120° C. for 20 min. After this time the solvent was evaporated to dryness in vacuo and the crude residue was purified by column chromatography (silicagel; EtOAc/methanol 100/0 to 95/5). The desired fractions were collected and the solvent was evaporated in vacuo to yield a mixture of the two intermediate compounds I-17 and I-17' that was used for the next reaction without further purification (0.18 g, 76%). $C_{24}H_{22}N_4O_4$.

Intermediate 18

2-{3-[4-(5-Methoxypyridin-2-ylmethoxy)-phenyl]-4-pyridin-4-yl-pyrazol-1-yl}-ethanol (I-18)

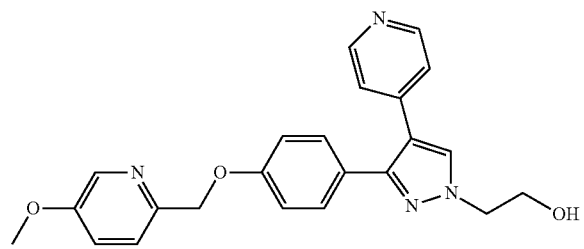 [SMILES: COc1ccc(COc2ccc(-c3nn(CCO)cc3-c3ccncc3)cc2)nc1]

To a stirred solution of the mixture of intermediates I-17 and I-17' (0.18 g, 0.418 mmol) in a mixture of DCM (4 mL) and methanol (1 mL) was added sodium borohydride (0.079 g, 2.09 mmol). The reaction mixture was stirred at room temperature for 3 h. The mixture was then quenched with water, extracted with more DCM, the organic solvent was dried over sodium sulphate and evaporated to dryness in vacuo. The crude residue was purified by column chromatography (silicagel; EtOAc/methanol from 100/0 to 90/10). The desired fractions were collected and evaporated in vacuo to yield intermediate compound 1-18 (0.09 g, 53.5%). The other regioisomer was not isolated from the chromatographic separation. $C_{23}H_{22}N_4O_3$.

LCMS: Rt 2.87, m/z 403 [M+H]$^+$ (method 2).

Intermediate 19

Methanesulfonic acid 2-{3-[4-(3,5-dimethylpyridin-2-ylmethoxy)-phenyl]-4-pyridin-4-yl-pyrazol-1-yl}-ethyl ester (I-19)

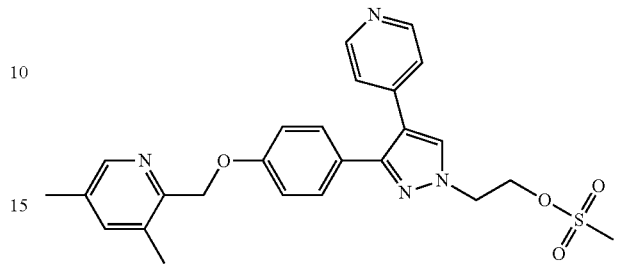

To a solution of intermediate I-16 (5 mg, 0.012 mmol) in DCM (1 mL) was added pyridine (11 µL) and this solution was stirred at 0° C. Methanesulfonic anhydride (16.5 mg, 0.095 mmol)) was then added and stirring was continued for 4 hours at 0° C. after which the solvent was evaporated by flushing with nitrogen. The crude mixture was redissolved in methanol (0.5 mL), diluted with water (4.5 mL) and passed through a $C_{18}$ SepPak® cartridge (Waters, Milford, Mass., USA) that was preconditioned with methanol (3 mL) and milliQ® water (6 mL). The cartridge was then rinsed three times with an additional volume of water (2 mL) to remove the unreacted methanesulfonic anhydride as much as possible. The product was eluted from the cartridge using acetonitrile (3 mL) and the solvents were evaporated under reduced pressure. Prior to evaporation of the solvents, HPLC analysis was performed to examine the conversion of the hydroxyl-precursor I-16 into its O-mesyl derivative I-19. This HPLC analysis was done on an analytical XTerra™ RP $C_{18}$ column (Waters), which was eluted with gradient mixtures of water and acetonitrile (0 min. 95:5 v/v, 25 min: 10:90 v/v, 30 min: 10:90 v/v, linear gradient) at a flow rate of 1 mL/min. The analysis showed that the average conversion rate was 98% (n=9). Residual water was removed by azeotropic distillation with acetonitrile and the mixture was dried overnight in the vacuum oven.

On the day of radiolabelling experiments, which is usually next day, this reaction product was dissolved in anhydrous DMF (1.5 mL) and used (0.3 mL) for direct nucleophilic radiofluorination. $C_{25}H_{26}N_4O_4S$.

Intermediate I-20

Methanesulfonic acid 2-{3-[4-(5-methoxypyridin-2-ylmethoxy)-phenyl]-4-pyridin-4-yl-pyrazol-1-yl}-ethyl ester (I-20)

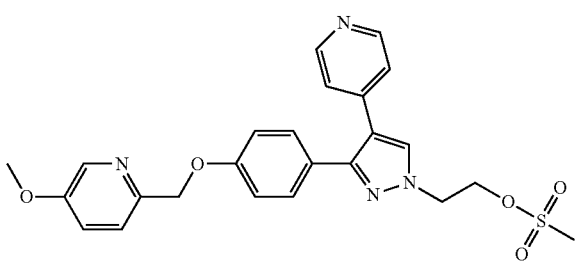

To a solution of intermediate I-18 (5 mg, 0.012 mmol) in DCM (1 mL) was added pyridine (11 μL) and this solution was stirred at 0° C. Methanesulfonic anhydride (16.5 mg, 0.095 mmol) was then added and stirring was continued for 4 hours at 0° C. after which the solvent was evaporated by flushing with nitrogen. The crude mixture was redissolved in methanol (0.5 mL), diluted with water (4.5 mL) and passed through a $C_{18}$ SepPak® cartridge (Waters, Milford, Mass., USA) that was preconditioned with methanol (3 mL) and milliQ® water (6 mL). The cartridge was then rinsed three times with an additional volume of water (2 mL) to remove the unreacted methanesulfonic anhydride as much as possible. The product was eluted from the cartridge using acetonitrile (3 mL) and the solvents were evaporated under reduced pressure. Prior to evaporation of the solvents, HPLC analysis was performed to examine the conversion of the hydroxyl-precursor I-18 into its O-mesyl derivative I-20. This HPLC analysis was done on an analytical XTerra™ RP $C_{18}$ column (Waters), which was eluted with gradient mixtures of water and acetonitrile (0 min: 95:5 v/v, 25 min: 10:90 v/v, 30 min: 10:90 v/v, linear gradient) at a flow rate of 1 mL/min. The analysis showed that the average conversion rate was 98% (n=9). Residual water was removed by azeotropic distillation with acetonitrile and the mixture was dried overnight in the vacuum oven. On the day of radiolabelling experiments, which is usually next day, this reaction product was dissolved in anhydrous DMF (1.5 mL) and used (0.3 mL) for direct nucleophilic radio fluorination. $C_{24}H_{24}N_4O_5S$.

B. Preparation of the Final Compounds

Example B1

2-[[4-[1-(2-fluoroethyl)-4-(4-pyridinyl)-1H-pyrazol-3-yl]phenoxy]methyl]-6-methyl-pyridine.dihydrochloride (B-1)

A mixture of intermediate compound I-5 (0.30 g, 0.876 mmol), 1-bromo-2-fluoroethane (0.083 mL, 1.051 mmol) and cesium carbonate (0.86 g, 2.63 mmol) in DMF (5 mL) was heated in a microwave oven at 150° C. for 10 min. After this time the reaction mixture was quenched with water and extracted with EtOAc. The organic layer was dried over sodium sulphate and the solvent was evaporated to dryness in vacuo. The crude residue was purified by column chromatography (silicagel; EtOAc/methanol 100/0 to 90/10) to give a mixture of the two isomers. This mixture was further subjected to another column chromatography purification (silicagel; acetonitrile/methanol 100/0 to 95/5). The desired fractions were collected and evaporated in vacuo to yield the desired compound B-1 as an oil (0.15 g, 44.1%). Treatment of this oily compound with a solution of hydrogen chloride in isopropyl alcohol, followed by crystallization from diethyl ether/DCM afforded the hydrochloric acid salt of compound B-1 as a yellow solid. $C_{23}H_{21}FN_4O.2HCl$. LCMS: Rt 3.82, m/z 389 [M+H]$^+$ (method 3).

$^1$H NMR (400 MHz, DMSO-d6) δ ppm 2.66 (s, 3H), 4.56 (dt, J=28.0, 4.6 Hz, 2H), 4.88 (dt, J=47.2, 4.6 Hz, 2H), 5.37 (s, 2H), 7.15 (d, J=8.8 Hz, 2H), 7.44 (d, J=8.6 Hz, 2H), 7.57 (d, J=7.2 Hz, 1H), 7.67 (d, J=7.2 Hz, 1H), 7.80 (d, J=6.9 Hz, 2H), 8.13 (t, J=7.1 Hz, 1H), 8.71 (s, 1H), 8.74 (d, J=6.9 Hz, 2H).

The corresponding regioisomer 2-{4-[2-(2-fluoroethyl)-4-pyridin-4-yl-2H-pyrazol-3-yl]-phenoxymethyl}-6-methyl-pyridine (B-1') was also isolated from the chromatographic separation with 70% purity (0.15 g, 30.8%) as an oil. $C_{23}H_{21}FN_4O$.

Radiosynthesis: Production of [$^{18}$F]Fluoroethyl Bromide and [$^{18}$F]B-1

[$^{18}$F]fluoride ([$^{18}$F]F$^-$) was produced by an [$^{18}$O(p,n)$^{18}$F] reaction by irradiation of 1.95 mL of 97% enriched [$^{18}$O]H$_2$O (Rotem HYOX18, Rotem Industries, Beer Sheva, Israel) in a niobium target using 18 MeV protons from a Cyclone 18/9 cyclotron (Ion Beam Applications, Louvain-la-Neuve, Belgium). After irradiation for about 60 min, the resultant [$^{18}$F]F$^-$ was separated from [$^{18}$O]H$_2$O using a SepPak™ Light Accell plus QMA anion exchange cartridge (Waters), which was preconditioned by successive treatments with 0.5 M $K_2CO_3$ solution (10 mL) and water (2×10 mL). The [$^{18}$F]F$^-$ was then eluted from the cartridge into a conical reaction vial (1 mL) using a solution containing potassium carbonate (2.47 mg) and Kryptofix® 222 (27.92 mg) dissolved in $H_2O$/$CH_3CN$ (0.75 mL; 5:95 v/v). The solvents were evaporated at 110° C. by applying conventional heating for 2 min. After evaporation of the solvent, [$^{18}$F]F$^-$ was further dried by azeotropic distillation of traces of water using acetonitrile (1 mL) at a temperature of 110° C. until complete dryness.

A solution of 2-bromoethyl triflate (5 μL, IsoSciences, Pennsylvania, USA) in o-dichlorobenzene (0.7 mL) was added to the vial containing [$^{18}$F]F$^-$. The resulting [$^{18}$F]FEtBr was then distilled at 120° C. with a helium flow (3-4 mL/min) and bubbled into a second reaction vial containing the precursor I-5 (0.2 mg) and a small amount (1-3 mg) of $Cs_2CO_3$ in anhydrous DMF (0.2 mL). After distillation of a sufficient amount of radioactivity into the precursor solution, the reaction vial was closed and heated at 90° C. for 15 min. After the reaction, the crude mixture was diluted with 1.6 mL of water and injected onto the HPLC system consisting of a semi-preparative XBridge™ column ($C_{18}$, 5 μm, 4.6 mm×150 mm; Waters) that was eluted with a mixture of 0.05 M sodium acetate buffer pH 5.5 and EtOH (70:30 v/v) at a flow rate of 1 mL/min. UV detection of the HPLC eluate was performed at 254 nm. The radiolabelled product [$^{18}$F]B-1 was collected after about 37 min. (The undesired isomer elutes after about 45 min). On average 50 mCi (n=2) of purified [$^{18}$F]B-1 was collected in 1.5-2 mL volume (mobile phase). The collected peak corresponding to the [$^{18}$F]B-1 was then diluted with normal saline (Mini Plasco®, Braun, Melsungen, Germany) to reduce the ethanol concentration to <5% and sterile filtered through a 0.22 μm membrane filter (Millex®-GV, Millipore, Ireland). The purity of the radiotracer was analyzed using an analytical HPLC system consisting of an XBridge™ column ($C_{18}$, 3.5 μm, 3 mm×100 mm; Waters) eluted with a mixture of 0.05 M sodium acetate buffer pH 5.5 and acetonitrile (70:30 v/v) at a flow rate of 0.8 mL/min (Rt=7.5 min). [$^{18}$F]B-1 was synthesized in 57% radiochemical yield (relative to [$^{18}$F]FEtBr starting radioactivity n=2). The radiochemical purity as examined using the above described analytical HPLC system was >99%.

Example B2

2-[[4-[1-(3-fluoropropyl)-4-(4-pyridinyl)-1H-pyrazol-3-yl]phenoxy]methyl]-6-methyl-pyridine.hydrochloride (B-2)

A mixture of intermediate compound I-5 (0.30 g, 0.876 mmol), 3-fluoropropan-1-ol (0.103 g, 1.314 mmol), diisopropyl azodicarboxylate (0.261 mL, 1.314 mmol) and triphenylphosphine (0.345 g, 1.314 mmol) in THF (3 mL) was heated in a microwave oven at 120° C. for 20 min. After this time the solvent was evaporated to dryness in vacuo and the crude residue was purified by column chromatography (silicagel; acetonitrile/methanol 100/0 to 95/5). The desired fractions were collected and evaporated in vacuo to yield the desired compound B-2 as a colourless oil, which was converted into the corresponding hydrochloric acid salt (0.075 g, 19.5%) (exact stoechiometry unknown) as a white solid. $C_{24}H_{23}FN_4O.HCl$. LCMS: Rt 4.09, m/z 403 $[M+H]^+$ (method 3).

$^1$H NMR (500 MHz, DMSO-$d_6$) δ ppm 2.20-2.34 (m, 2H), 2.62 (s, 3H), 4.33 (t, J=6.9 Hz, 2H), 4.54 (ddd, J=47.3, 5.6, 5.5 Hz, 2H), 5.32 (s, 2H), 7.14 (d, J=8.7 Hz, 2H), 7.43 (d, J=8.7 Hz, 2H), 7.50 (d, J=6.6 Hz, 1H), 7.60 (d, J=6.4 Hz, 1H), 7.78 (d, J=6.6 Hz, 2H), 8.05 (br. s., 1H), 8.69 (s, 1H), 8.73 (d, J=6.4 Hz, 2H).

The corresponding regioisomer 2-{4-[2-(3-fluoropropyl)-4-pyridin-4-yl-2H-pyrazol-3-yl]-phenoxymethyl}-6-methyl-pyridine (B-2') was also isolated from the chromatographic separation and converted into its corresponding hydrochloric acid salt (0.07 g, 18.2%) as a white powder. $C_{24}H_{23}FN_4O$.

Example B3

2-[[4-[1-(2-fluoroethyl)-4-(4-pyridinyl)-1H-pyrazol-3-yl]phenoxy]methyl]-3,5-dimethyl-pyridine.succinate (B-3)

A mixture of intermediate compound 1-7 (0.20 g, 0.706 mmol), 3,5-dimethyl-2-hydroxymethylpyridine (0.126 g, 0.918 mmol), diisopropyl azodicarboxylate (0.211 g, 0.918 mmol) and triphenylphosphine (0.241 g, 0.918 mmol) in THF (4 mL) was heated in a microwave oven at 120° C. for 15 min. After this time the mixture was quenched with a saturated aqueous solution of sodium carbonate and extracted with DCM. The organic solvent was dried over sodium sulphate and evaporated to dryness in vacuo. The crude residue was purified by column chromatography (silicagel; EtOAc/methanol 100/0 to 95/5). The desired fractions were collected and the solvent was evaporated in vacuo to yield compound B-3 as a colourless oil. The residue was dissolved in methanol (2 mL) and a solution of succinic acid (0.073 g, 0.619 mmol) in methanol (2 mL) was slowly added. The solvent was evaporated to dryness and the solid residue was washed several times with diethyl ether, yielding the succinic acid salt of final compound B-3 (0.295 g, 80.3%) as a white solid. $C_{24}H_{23}FN_4O.C_4H_6O_4$. LCMS: Rt 3.08, m/z 403 $[M+H]^+$ (method 7).

$^1$H NMR (400 MHz, DMSO-$d_6$) δ ppm 2.28 (s, 3H), 2.35 (s, 3H), 2.42 (s, 4H), 4.49 (dt, J=27.7, 4.7 Hz, 2H), 4.85 (dt, J=47.2, 4.6 Hz, 2H), 5.16 (s, 2H), 7.05 (d, J=8.8 Hz, 2H), 7.23 (d, J=6.0 Hz, 2H), 7.32 (d, J=8.8 Hz, 2H), 7.48 (s, 1H), 8.23 (s, 2H), 8.46 (d, J=5.8 Hz, 2H), 12.15 (br. s., 2H).

Radiosynthesis: Production of [$^{18}$F]fluoride and [$^{18}$F]B-3

[$^{18}$F]fluoride ([$^{18}$F]F$^-$) was produced in a similar way as described above for the radiosynthesis of [$^{18}$F]FEtBr with the modification that the [$^{18}$F]F$^-$ was eluted from the cartridge using a solution of 0.45 mL of the Kryptofix® 222/$K_2CO_3$ solution and 0.3 mL of acetonitrile.

The radiolabeling precursor I-19 (~0.6 mg in 0.3 mL DMF) was added to the dried [$^{18}$F]F$^-$/$K_2CO_3$/Kryptofix® 222 complex and the nucleophilic substitution reaction was carried out by conventional heating at 90° C. for 15 min. After the reaction, the crude mixture was diluted with 1.4 mL of water and injected onto the HPLC system consisting of a semi-preparative XBridge™ column ($C_{18}$, 5 μm, 4.6 mm×150 mm; Waters) that was eluted with a mixture of 0.05 M sodium acetate buffer pH 5.5 and EtOH (65:35 v/v) at a flow rate of 1 mL/min. UV detection of the HPLC eluate was performed at 254 nm. The radiolabelled product [$^{18}$F]B-3 was collected after about 26 min. On average 100 mCi (n=7, min 60 mCi, max 180 mCi) of purified [$^{18}$F]B-3 was collected in 1.5-2 mL volume (mobile phase). The collected peak corresponding to the [$^{18}$F]B-3 was then diluted with normal saline (Mini Plasco®, Braun, Melsungen, Germany) to reduce the ethanol concentration to <5% and sterile filtered through a 0.22 μm membrane filter (Millex®-GV, Millipore, Ireland). The purity of the radiotracer was analyzed using an analytical HPLC system consisting of an XBridge™ column ($C_{18}$, 3.5 nm, 3 mm×100 mm; Waters) eluted with a mixture of 0.05 M sodium acetate buffer pH 5.5 and acetonitrile (65:35 v/v) at a flow rate of 0.8 mL/min (Rt=5.6 min) UV detection of the HPLC eluate was performed at 254 nm. [$^{18}$F]B-3 was synthesized in 16% radiochemical yield (relative to starting radioactivity [$^{18}$F]F$^-$, n=7). The radiochemical purity as examined using the above described analytical HPLC system was >98%. The average specific radioactivity of the tracer as examined using the above described analytical HPLC system was found to be 176 GBq/μmol (4764 Ci/mmol, n=7) at the end of synthesis (EOS).

Example B4

2-[[4-[1-(2-fluoroethyl)-4-(4-pyridinyl)-1H-pyrazol-3-yl]phenoxy]methyl]-5-methoxy-pyridine (B-4)

A mixture of intermediate compound 1-7 (0.13 g, 0.344 mmol), (5-methoxypyridin-2-yl)methanol (0.072 g, 0.516 mmol) prepared as described in Bioorg. Med. Chem. 2005, 13, 6763-6770, diisopropyl azodicarboxylate (0.10 mL, 0.516 mmol) and triphenylphosphine (0.135 g, 0.516 mmol) in THF (4 mL) was heated in a microwave oven at 120° C. for 20 min. After this time the mixture was quenched with a saturated aqueous solution of sodium carbonate, extracted with EtOAc, dried over sodium sulphate and evaporated to dryness in vacuo. The crude residue was purified by column chromatography (silicagel; EtOAc/methanol 100/0 to 95/5). The desired fractions were collected and the solvent was evaporated in vacuo to yield compound B-4 (0.12 g, 86.2%) as a white solid. $C_{23}H_{21}FN_4O_2$. LCMS: Rt 2.7, m/z 405 $[M+H]^+$ (method 7).

$^1$H NMR (400 MHz, CDCl$_3$) δ ppm 3.87 (s, 3H), 4.47 (dt, J=27.0, 4.7 Hz, 2H), 4.84 (dt, J=46.9, 4.6 Hz, 2H), 5.17 (s, 2H), 6.97 (d, J=8.8 Hz, 2H), 7.18 (d, J=6.0 Hz, 2H), 7.22 (dd, J=8.6, 3.0 Hz, 1H), 7.39 (d, J=8.8 Hz, 2H), 7.44 (d, J=8.6 Hz, 1H), 7.70 (s, 1H), 8.30 (d, J=3.0 Hz, 1H), 8.48 (d, J=6.2 Hz, 2H).

Radiosynthesis: Production of [$^{18}$F]fluoride and [$^{18}$F]B-4

[$^{18}$F]fluoride ([$^{18}$F]F$^-$) was produced exactly in the same way as described above for the radiosynthesis of compound [$^{18}$F]B-3.

The radiolabeling precursor I-20 (~0.6 mg in 0.3 mL DMF) was added to the dried [$^{18}$F]F$^-$/$K_2CO_3$/Kryptofix® 222 complex and the nucleophilic substitution reaction was carried out by conventional heating at 90° C. for 10 min. After the reaction, the crude mixture was diluted with 1.4 mL of water and injected onto the HPLC system consisting of a semi-preparative XBridge™ column ($C_{18}$, 5 μm, 4.6 mm×150 mm; Waters) that was eluted with a mixture of 0.05 M sodium acetate buffer pH 5.5 and EtOH (70:30 v/v) at a flow rate of 1 mL/min. UV detection of the HPLC eluate was performed at 254 nm. The radiolabelled product [$^{18}$F]B-4 was collected after about 35 min. Typically, about 90 mCi of purified [$^{18}$F] B-4 was collected in 1.5-2 mL volume (mobile phase). The collected peak corresponding to the [$^{18}$F]B-4 was then diluted with normal saline (Mini Plasco®, Braun, Melsungen, Germany) to reduce the ethanol concentration to <5% and sterile filtered through a 0.22 μm membrane filter (Millex®-GV, Millipore, Ireland). The purity of the radiotracer was analyzed using an analytical HPLC system consisting of an XBridge™ column ($C_{18}$, 3.5 μm, 3 mm×100 mm; Waters) eluted with a mixture of 0.05 M sodium acetate buffer pH 5.5 and acetonitrile (70:30 v/v) at a flow rate of 0.8 mL/min (Rt=7.2 min) UV detection of the HPLC eluate was performed at 254 nm. [$^{18}$F]B-4 was synthesized in 15% radiochemical yield (relative to starting radioactivity [$^{18}$F]F$^-$, n=2). The radiochemical purity as examined using the above described analytical HPLC system was >99%. The average specific radioactivity of the tracer as examined using the above described analytical HPLC system was found to be 141 GBq/μmol (3800 Ci/mmol, n=2) at the EOS.

Example B5

5-methoxy-2-[[4-[4-(4-pyridinyl)-1-(2,2,2-trifluoroethyl)-1H-pyrazol-3-yl]phenoxy]methyl]-pyridine (B-5)

A mixture of intermediate compound I-10 (0.15 g, 0.47 mmol), (5-methoxypyridin-2-yl)methanol (0.098 g, 0.70 mmol), diisopropyl azodicarboxylate (0.14 mL, 0.70 mmol) and triphenylphosphine (0.185 g, 0.70 mmol) in THF (3 mL) was heated in a microwave oven at 120° C. for 20 min. After this time the mixture was quenched with a saturated aqueous solution of sodium carbonate and extracted with EtOAc. The organic solvent was dried over sodium sulphate and evaporated to dryness in vacuo. The crude residue was purified by column chromatography (silicagel; EtOAc/methanol 100/0 to 95/5). The desired fractions were collected and the solvent was evaporated in vacuo to yield compound B-5 (0.11 g, 53.2%) as a colourless oil that solidified on standing, affording a white solid. $C_{23}H_{19}F_3N_4O_2$. LCMS: Rt 4.27, m/z 441 [M+H]$^+$ (method 2).
$^1$H NMR (400 MHz, CDCl$_3$) δ ppm 3.87 (s, 3H), 4.77 (q, J=8.3 Hz, 2H), 5.17 (s, 2H), 6.97 (d, J=9.0 Hz, 2H), 7.19 (d, J=6.2 Hz, 2H), 7.23 (dd, J=8.6, 3.0 Hz, 1H), 7.38 (d, J=8.8 Hz, 2H), 7.44 (d, J=8.6 Hz, 1H), 7.71 (s, 1H), 8.30 (d, J=2.8 Hz, 1H), 8.51 (d, J=6.0 Hz, 2H).

Example B6

2-bromo-6-[[4-[1-(2-fluoroethyl)-4-(4-pyridinyl)-1H-pyrazol-3-yl]phenoxy]methyl]-pyridine.0.75 succinate (B-6)

A mixture of intermediate compound I-7 (0.30 g, 1.06 mmol), (6-bromo-pyridin-2-yl)methanol (0.30 g, 1.59 mmol), diisopropyl azodicarboxylate (0.315 mL, 1.59 mmol) and triphenylphosphine (0.417 g, 1.59 mmol) in THF (5 mL) was heated in a microwave oven at 100° C. for 30 min. After this time the mixture was quenched with a saturated aqueous solution of sodium carbonate and extracted with DCM. The organic solvent was dried over sodium sulphate and evaporated to dryness in vacuo. The crude residue was purified by column chromatography (silicagel; first EtOAc/heptane 70/30 and then diethyl ether/DCM 70/30). The desired fractions were collected and the solvent was evaporated in vacuo to yield compound B-6 (0.30 g, 53.1%) as a colourless oil. An amount of compound B-6 (0.08 g) was converted into the corresponding succinic acid salt in a similar way as it is described above for final compound B-3, yielding final compound B-6 as a white solid. $C_{22}H_{18}BrFN_4O.0.75C_4H_6O_4$. LCMS: Rt 3.22, m/z 453 [M+H]$^+$ (method 7).

$^1$H NMR (400 MHz, DMSO-d$_6$) δ ppm 2.42 (s, 3H), 4.50 (dt, J=27.7, 4.6 Hz, 2H), 4.85 (dt, J=47.2, 4.7 Hz, 2H), 5.20 (s, 2H), 7.06 (d, J=8.8 Hz, 2H), 7.22 (d, J=6.0 Hz, 2H), 7.35 (d, J=8.8 Hz, 2H), 7.59 (d, J=7.4 Hz, 1H), 7.63 (d, J=7.9 Hz, 1H), 7.82 (t, J=7.7 Hz, 1H), 8.24 (s, 1H), 8.46 (d, J=6.0 Hz, 2H), 12.16 (br. s., 1.5H).

Example B7

2-[[4-[1-(2-fluoroethyl)-4-(4-pyridinyl)-1H-pyrazol-3-yl]phenoxy]methyl]-6-(trifluoromethyl)-pyridine (B-7)

Compound B-6 (0.45 g, 0.725 mmol) was dissolved in DMF (3 mL) and then (fluorosulfonyl)difluoroacetic acid methyl ester (0.464 mL, 3.62 mmol) and cuprous iodide (0.69 g, 3.62 mmol) were added to the solution. The reaction mixture was heated at 120° C. in a sealed tube for 2 h. The reaction mixture was quenched with aqueous 1 M sodium hydroxide and extracted with DCM. The organic solvent was dried over sodium sulphate and evaporated to dryness in vacuo. The residue was purified by column chromatography (silicagel; EtOAc/heptane 70/30 to 100/0). The desired fractions were collected and the solvent was evaporated in vacuo to give the desired compound as a yellow oil, which contained triphenylphosphine oxide as the main impurity. The crude compound was further purified by preparative HPLC (C18 XBridge 30×100; aq. ammonium carbonate pH 9/acetonitrile gradient from 80/20 to 0/100) affording B-7 as a colourless oil. The compound was made solid by addition of diethyl ether/heptane and finally was recrystallized from diisopropyl ether yielding final compound B-7 (0.023 g, 7.2%) as a white solid. $C_{23}H_{18}F_4N_4O$. LCMS: Rt 3.73, m/z 443 [M+H]$^+$ (method 4).
$^1$H NMR (400 MHz, DMSO-d$_6$) δ ppm 4.50 (dt, J=27.8, 4.7 Hz, 2H), 4.85 (dt, J=47.2, 4.6 Hz, 2H), 5.31 (s, 2H), 7.09 (d, J=8.8 Hz, 2H), 7.22 (d, J=6.0 Hz, 2H), 7.35 (d, J=8.8 Hz, 2H), 7.89 (d, J=7.9 Hz, 1H), 7.89 (d, J=7.6 Hz, 1H), 8.18 (t, J=7.9 Hz, 1H), 8.24 (s, 1H), 8.46 (d, J=6.0 Hz, 2H).

Example B8

2-Cyclopropyl-6-[[4-[1-(2-fluoroethyl)-4-(4-pyridinyl)-1H-pyrazol-3-yl]phenoxy]methyl]-pyridine.succinate (B-8)

A mixture of compound B-6 (0.14 g, 0.263 mmol), cyclopropyl-boronic acid (0.029 g, 0.341 mmol) and palladium (0) tetrakis(triphenylphosphine) (0.015 g, 0.013 mmol) in a mixture of aq. sodium carbonate/dioxane 1:1 (5 mL) was heated in a microwave oven at 130° C. for 15 min. After cooling to room temperature, the crude mixture was diluted with water and extracted with DCM. The organic solvent was dried over sodium sulphate and evaporated to dryness in vacuo. The residue was purified by column chromatography (silicagel; EtOAc), the desired fractions were collected and the solvent was evaporated in vacuo to give the desired compound as a colourless oil, which contained triphenylphosphine oxide as the main impurity. The compound was further purified by preparative HPLC (C18 XBridge 19×100; aq. ammonium carbonate pH 9/acetonitrile gradient from 80/20 to 0/100) affording B-8 as a colourless oil. The residue was dissolved in methanol (2 mL) and a solution of succinic acid (0.017 g, 0.144 mmol) in methanol (1 mL) was slowly added. The solvent was evaporated to dryness and the residue was treated with DCM/diisopropyl ether, yielding the succinic acid salt of final compound B-8 (0.076 g, 54.4%) as a white solid.

$C_{25}H_{23}FN_4O \cdot C_4H_6O_4$. LCMS: Rt 4.19, m/z 415 [M+H]$^+$ (method 2).

$^1$H NMR (400 MHz, DMSO-d$_6$) δ ppm 0.87-0.99 (m, 4H), 2.05-2.16 (m, 1H), 2.42 (s, 4H), 4.49 (dt, J=27.7, 4.6 Hz, 2H), 4.85 (dt, J=47.2, 4.7 Hz, 2H), 5.10 (s, 2H), 7.04 (d, J=9.0 Hz, 2H), 7.20-7.24 (m, 3H), 7.26 (d, J=7.4 Hz, 1H), 7.33 (d, J=8.8 Hz, 2H), 7.68 (t, J=7.7 Hz, 1H), 8.24 (s, 1H), 8.45 (d, J=6.2 Hz, 2H), 12.17 (br. s., 1H).

The following compounds were prepared following one of the synthesis methods described above.

3-methoxy-2-[[4-[4-(4-pyridinyl)-1-(2,2,2-trifluoroethyl)-1H-pyrazol-3-yl]phenoxy]methyl]-pyridine (B-9)

Following the procedure for the preparation of compound B-5 but substituting (5-methoxypyridin-2-yl)methanol for (3-methoxypyridin-2-yl)methanol provided final compound B-9 (58%) as a white solid that was further crystallized from diisopropyl ether. $C_{23}H_{19}F_3N_4O_2$. LCMS: Rt 3.01, m/z 441 [M+H]$^+$ (method 7)).

$^1$H NMR (400 MHz, CDCl$_3$) δ ppm 3.89 (s, 3H), 4.77 (q, J=8.3 Hz, 2H), 5.26 (s, 2H), 7.02-7.07 (m, 2H), 7.17-7.21 (m, 2H), 7.23 (dd, J=8.3, 1.6 Hz, 1H), 7.27 (dd, J=8.3, 4.6 Hz, 1H), 7.34-7.41 (m, 2H), 7.70 (s, 1H), 8.25 (dd, J=4.4, 1.6 Hz, 1H), 8.49-8.53 (m, 2H).

3-(2-fluoroethoxy)-2-[[4-[4-(4-pyridinyl)-1-(2,2,2-trifluoroethyl)-1H-pyrazol-3-yl]phenoxy]methyl]-pyridine.succinate (B-10)

Following the procedure for the preparation of compound B-5 but substituting (5-methoxypyridin-2-yl)methanol for [3-(2-fluoroethoxy)-pyridin-2-yl]-methanol provided final compound B-10 that was converted into the corresponding succinic acid salt, in a similar way as it is described above for final compound B-3, which was crystallized from diethyl ether yielding the succinic acid salt of final compound B-10 (33.8%) as a white solid. $C_{24}H_{20}F_4N_4O_2 \cdot C_4H_6O_4$. LCMS: Rt 2.96, m/z 473 [M+H]$^+$ (method 7).

$^1$H NMR (500 MHz, DMSO-d$_6$) δ ppm 2.40 (s, 4H), 4.31-4.42 (m, 2H), 4.67-4.82 (m, 2H), 5.21 (q, J=9.0 Hz, 2H), 5.18 (s, 2H), 7.05 (br. d, J=8.7 Hz, 2H), 7.22-7.26 (m, 2H), 7.31 (br. d, J=8.7 Hz, 2H), 7.40 (dd, J=8.4, 4.9 Hz, 1H), 7.56 (d, J=8.4 Hz, 1H), 8.19 (dd, J=4.5, 1.0 Hz, 1H), 8.28 (s, 1H), 8.45-8.52 (m, 2H), 12.19 (br. s., 2H).

5-(2-fluoroethoxy)-2-[[4-[4-(4-pyridinyl)-1-(2,2,2-trifluoroethyl)-1H-pyrazol-3-yl]phenoxy]methyl]-pyridine (B-11)

Following the procedure for the preparation of compound B-5 but substituting (5-methoxypyridin-2-yl)methanol for [5-(2-fluoroethoxy)-pyridin-2-yl]-methanol provided final compound B-11 (20.3%) as a white solid after crystallization from diisopropyl ether/heptanes. $C_{24}H_{20}F_4N_4O_2$. LCMS: Rt 3.9, m/z 473 [M+H]$^+$ (method 5).

$^1$H NMR (400 MHz, CDCl$_3$) δ ppm 4.22-4.34 (m, 2H), 4.70-4.87 (m, 2H), 4.77 (q, J=8.3 Hz, 2H), 5.18 (s, 2H), 6.94-7.00 (m, 2H), 7.17-7.21 (m, 2H), 7.27 (dd, J=8.6, 2.8 Hz, 1H), 7.35-7.41 (m, 2H), 7.46 (d, J=8.6 Hz, 1H), 7.71 (s, 1H), 8.33 (d, J=2.8 Hz, 1H), 8.49-8.54 (m, 2H).

2-[[4-[1-(3-fluoropropyl)-4-(4-pyridinyl)-1H-pyrazol-3-yl]phenoxy]methyl]-3-methoxy-pyridine (B-12)

Following the procedure for the preparation of compound B-5, but substituting (5-methoxypyridin-2-yl)methanol for (3-methoxypyridin-2-yl)methanol and 1-10 for intermediate compound 1-8, provided final compound B-12 (40%) as a white solid.

$C_{24}H_{23}FN_4O_2$. LCMS: Rt 3.78, m/z 419 [M+H]$^+$ (method 2).

$^1$H NMR (500 MHz, CDCl$_3$) δ ppm 2.34 (dquin, J=26.9, 6.0, 6.0, 6.0, 6.0 Hz, 2H), 3.89 (s, 3H), 4.33 (t, J=6.8 Hz, 2H), 4.51 (dt, J=47.1, 5.5 Hz, 2H), 5.25 (s, 2H), 7.01-7.06 (m, 2H), 7.16-7.20 (m, 2H), 7.23 (dd, J=8.4, 1.2 Hz, 1H), 7.27 (dd, J=8.4, 4.7 Hz, 1H), 7.34-7.41 (m, 2H), 7.63 (s, 1H), 8.25 (dd, J=4.5, 1.6 Hz, 1H), 8.45-8.50 (m, 2H).

3-(2-fluoroethoxy)-2-[[4-[1-(3-fluoropropyl)-4-(4-pyridinyl)-1H-pyrazol-3-yl]phenoxy]methyl]pyridine.succinate (B-13)

Following the procedure for the preparation of compound B-5, but substituting (5-methoxypyridin-2-yl)methanol for [3-(2-fluoroethoxy)-pyridin-2-yl]-methanol and 1-10 for intermediate compound 1-8, provided final compound B-13 that was converted into the corresponding succinic acid salt, in a similar way as it is described above for final compound B-3, which was crystallized from diethyl ether/diisopropyl ether yielding the succinic acid salt of final compound B-13 (39.2%) as a white solid.

$C_{25}H_{24}F_2N_4O_2 \cdot C_4H_6O_4$. LCMS: Rt 2.75, m/z 451 [M+H]$^+$ (method 7).

$^1$H NMR (500 MHz, DMSO-d$_6$) δ ppm 2.25 (dquin, J=26.3, 6.4, 6.4, 6.4, 6.4 Hz, 2H), 2.42 (s, 4H), 4.27 (t, J=6.9 Hz, 2H), 4.37 (dt, J=29.8, 3.8 Hz, 2H), 4.53 (dt, J=47.4, 5.7 Hz, 2H), 4.75 (dt, J=47.7, 3.5 Hz, 2H), 5.18 (s, 2H), 7.04 (br. d, J=8.7 Hz, 2H), 7.19-7.25 (m, 2H), 7.31 (br. d, J=8.7 Hz, 2H), 7.40 (dd, J=8.4, 4.6 Hz, 1H), 7.56 (d, J=8.1 Hz, 1H), 8.19 (d, J=4.6 Hz, 1H), 8.23 (s, 1H), 8.45 (br. d, J=6.1 Hz, 2H), 12.17 (br. s., 2H).

2-[[4-[1-(3-fluoropropyl)-4-(4-pyridinyl)-1H-pyrazol-3-yl]phenoxy]methyl]-5-methoxy-pyridine.0.5 succinate (B-14)

Following the procedure for the preparation of compound B-5, but substituting (5-methoxypyridin-2-yl)methanol for (5-methoxypyridin-2-yl)methanol and 1-10 for intermediate compound 1-8, provided final compound B-14 as a colourless oil, that was converted into the corresponding succinic acid salt, in a similar way as it is described above for final compound B-3, which was crystallized from diethyl ether yielding the succinic acid salt of final compound B-14 (25.6%) as a white solid.

$C_{24}H_{23}FN_4O_2 \cdot 0.5 C_4H_6O_4$. LCMS: Rt 3.97, m/z 419 [M+H]$^+$ (method 2).

$^1$H NMR (400 MHz, DMSO-d$_6$) δ ppm 2.24 (dquin, J=26.4, 6.2 Hz, 2H), 2.41 (s, 2H), 3.84 (s, 3H), 4.27 (t, J=6.9 Hz, 2H), 4.52 (dt, J=47.2, 5.7 Hz, 2H), 5.11 (s, 2H), 7.03 (br. d, J=8.8 Hz, 2H), 7.17-7.25 (m, 2H), 7.31 (br. d, J=8.8 Hz, 2H), 7.43 (dd, J=8.3, 3.0 Hz, 1H), 7.50 (d, J=8.6 Hz, 1H), 8.23 (s, 1H), 8.29 (d, J=2.8 Hz, 1H), 8.40-8.48 (m, 2H), 12.18 (br. s., 1H).

5-(2-fluoroethoxy)-2-[[4-[1-(3-fluoropropyl)-4-(4-pyridinyl)-1H-pyrazol-3-yl]phenoxy]methyl]-pyridine (B-15)

Following the procedure for the preparation of compound B-5, but substituting (5-methoxypyridin-2-yl)methanol for [5-(2-fluoroethoxy)-pyridin-2-yl]-methanol and 1-10 for intermediate compound 1-8, provided compound B-15 as a colourless oil that solidified on standing. Finally the compound was washed with diisopropyl ether to yield final compound B-15 (35.8%) as a white solid. $C_{25}H_{24}F_2N_4O_2$. LCMS: Rt 3.69, m/z 451 [M+H]$^+$ (method 5).

$^1$H NMR (500 MHz, CDCl$_3$) δ ppm 2.34 (dquin, J=26.9, 6.2, 6.2, 6.2, 6.2 Hz, 2H), 4.23-4.33 (m, 2H), 4.33 (t, J=6.7 Hz, 2H), 4.51 (dt, J=47.4, 5.7 Hz, 2H), 4.71-4.86 (m, 2H), 5.17 (s, 2H), 6.94-6.99 (m, 2H), 7.18 (br. d, J=6.1 Hz, 2H), 7.27 (dd, J=8.7, 2.9 Hz, 1H), 7.35-7.41 (m, 2H), 7.46 (d, J=8.7 Hz, 1H), 7.64 (s, 1H), 8.33 (br. d, J=2.9 Hz, 1H), 8.48 (br. d, J=6.1 Hz, 2H).

2-[[4-[1-(2-fluoroethyl)-4-(4-pyridinyl)-1H-pyrazol-3-yl]phenoxy]methyl]-3-methoxy-pyridine.succinate (B-16)

Following the procedure for the preparation of compound B-4 but substituting (5-methoxypyridin-2-yl)methanol for (3-methoxypyridin-2-yl)methanol provided compound B-16 that was converted into the corresponding succinic acid salt, in a similar way as it is described above for final compound B-3, which was crystallized from diethyl ether yielding the succinic acid salt of final compound B-16 (32.5%) as a white solid. $C_{23}H_{21}FN_4O_2 \cdot C_4H_6O_4$. LCMS: Rt 3.52, m/z 405 [M+H]$^+$ (method 2).

$^1$H NMR (400 MHz, DMSO-d$_6$) δ ppm 2.41 (s, 4H), 3.86 (s, 3H), 4.49 (dt, J=27.7, 4.8 Hz, 2H), 4.85 (dt, J=47.2, 4.8 Hz, 2H), 5.13 (s, 2H), 7.03 (br. d, J=8.8 Hz, 2H), 7.18-7.26 (m, 2H), 7.31 (br. d, J=8.8 Hz, 2H), 7.41 (dd, J=8.3, 4.6 Hz, 1H), 7.52 (dd, J=8.4, 1.0 Hz, 1H), 8.16 (dd, J=4.6, 1.4 Hz, 1H), 8.23 (s, 1H), 8.43-8.48 (m, 2H), 12.16 (br. s, 2H).

3-(2-fluoroethoxy)-2-[[4-[1-(2-fluoroethyl)-4-(4-pyridinyl)-1H-pyrazol-3-yl]phenoxy]methyl]pyridine.succinate (B-17)

Following the procedure for the preparation of compound B-4 but substituting (5-methoxypyridin-2-yl)methanol for [3-(2-fluoroethoxy)-pyridin-2-yl]-methanol provided compound B-17 that was converted into the corresponding succinic acid salt, in a similar way as it is described above for final compound B-3, which was crystallized from diethyl ether yielding the succinic acid salt of final compound B-17 (78.3%) as a white solid. $C_{24}H_{22}F_2N_4O_2 \cdot C_4H_6O_4$. LCMS: Rt 2.52, m/z 437 [M+H]$^+$ (method 7).

$^1$H NMR (500 MHz, DMSO-d$_6$) δ ppm 2.42 (s, 4H), 4.32-4.41 (m, 2H), 4.49 (dt, J=27.7, 4.6 Hz, 2H), 4.68-4.81 (m, 2H), 4.85 (dt, J=47.1, 4.9 Hz, 2H), 5.18 (s, 2H), 7.04 (br. d, J=8.7 Hz, 2H), 7.21-7.25 (m, 2H), 7.32 (br. d, J=9.0 Hz, 2H), 7.40 (dd, J=8.4, 4.6 Hz, 1H), 7.56 (d, J=8.1 Hz, 1H), 8.19 (d, J=4.6 Hz, 1H), 8.23 (s, 1H), 8.44-8.48 (m, 2H), 12.16 (br. s., 2H).

3-fluoro-2-[[4-[1-(2-fluoroethyl)-4-(4-pyridinyl)-1H-pyrazol-3-yl]phenoxy]methyl]-pyridine.1.2 succinate (B-18)

Following the procedure for the preparation of compound B-6 but substituting (6-bromopyridin-2-yl)methanol for (3-fluoropyridin-2-yl)methanol provided compound B-18 that was converted into the corresponding succinic acid salt, in a similar way as it is described above for final compound B-3, which was crystallized from diethyl ether yielding the succinic acid salt of final compound B-18 (23.9%) as a white solid.
$C_{22}H_{18}F_2N_4O \cdot 1.2 C_4H_6O_4$. LCMS: Rt 2.63, m/z 393 [M+H]$^+$ (method 7).

$^1$H NMR (400 MHz, DMSO-d$_6$) δ ppm 2.41 (s, 4.8H), 4.50 (dt, J=27.7, 4.6 Hz, 2H), 4.85 (dt, J=46.9, 4.9 Hz, 2H), 5.25 (d, J=2.1 Hz, 2H), 7.04-7.10 (m, 2H), 7.19-7.25 (m, 2H), 7.30-7.37 (m, 2H), 7.54 (dt, J=8.5, 4.4 Hz, 1H), 7.78-7.84 (m, 1H), 8.24 (s, 1H), 8.42-8.51 (m, 3H), 12.26 (br. s., 2.4H).

5-(2-fluoroethoxy)-2-[[4-[1-(2-fluoroethyl)-4-(4-pyridinyl)-1H-pyrazol-3-yl]phenoxy]methyl]-pyridine (B-19)

Following the procedure for the preparation of compound B-4, but substituting (5-methoxypyridin-2-yl)methanol for [5-(2-fluoroethoxy)-pyridin-2-yl]-methanol provided compound B-19 (56.3%) as a white solid after treatment with diisopropyl ether. $C_{24}H_{22}F_2N_4O_2$. LCMS: Rt 3.48, m/z 437 [M+H]$^+$ (method 5).

$^1$H NMR (400 MHz, CDCl$_3$) δ ppm 4.22-4.34 (m, 2H), 4.47 (dt, J=27.1, 4.9 Hz, 2H), 4.70-4.87 (m, 2H), 4.84 (dt, J=46.9, 4.6 Hz, 2H), 5.18 (s, 2H), 6.97 (br. d, J=8.8 Hz, 2H), 7.16-7.21 (m, 2H), 7.27 (dd, J=8.6, 2.8 Hz, 1H), 7.36-7.42 (m, 2H), 7.46 (d, J=8.6 Hz, 1H), 7.70 (s, 1H), 8.33 (d, J=2.8 Hz, 1H), 8.45-8.52 (m, 2H).

5-bromo-2-[[4-[1-(2-fluoroethyl)-4-(4-pyridinyl)-1H-pyrazol-3-yl]phenoxy]methyl]-pyridine (B-20)

Following the procedure for the preparation of compound B-6 but substituting (6-bromopyridin-2-yl)methanol for (5-bromopyridin-2-yl)methanol provided compound B-20 (15.6%) as a white solid after treatment with diethyl ether. $C_{22}H_{18}BrFN_4O$.

LCMS: Rt 3.29, m/z 453 [M+H]$^+$ (method 7).

$^1$H NMR (400 MHz, CDCl$_3$) δ ppm 4.47 (dt, J=27.0, 4.6 Hz, 2H), 4.84 (dt, J=46.9, 4.9 Hz, 2H), 5.18 (s, 2H), 6.93-6.98 (m, 2H), 7.17-7.20 (m, 2H), 7.38-7.42 (m, 2H), 7.45 (dd, J=8.3, 0.7 Hz, 1H), 7.70 (d, J=0.5 Hz, 1H), 7.85 (dd, J=8.3, 2.3 Hz, 1H), 8.47-8.51 (m, 2H), 8.66 (dd, J=2.3, 0.5 Hz, 1H).

6-[[4-[1-(2-fluoroethyl)-4-(4-pyridinyl)-1H-pyrazol-3-yl]phenoxy]methyl]-3-pyridinecarbonitrile (B-21)

Following the procedure for the preparation of compound B-6 but substituting (6-bromopyridin-2-yl)methanol for 6-(hydroxymethyl)nicotinonitrile provided compound B-21 (39.4%) as a white solid. $C_{23}H_{18}FN_5O$. LCMS: Rt 3.11, m/z 400 [M+H]$^+$ (method 4).

$^1$H NMR (500 MHz, CDCl$_3$) δ ppm 4.48 (dt, J=27.2, 4.6 Hz, 2H), 4.85 (dt, J=46.8, 4.6 Hz, 2H), 5.28 (s, 2H), 6.96 (br. d, J=9.0 Hz, 2H), 7.16-7.21 (m, 2H), 7.39-7.45 (m, 2H), 7.72 (d, J=8.4 Hz, 1H), 7.71 (s, 1H), 8.00 (dd, J=8.1, 2.0 Hz, 1H), 8.49 (br. d, J=6.1 Hz, 2H), 8.87 (d, J=1.4 Hz, 1H).

2-[[4-[1-(2-fluoroethyl)-4-(4-pyridinyl)-1H-pyrazol-3-yl]phenoxy]methyl]-5-(trifluoromethyl)-pyridine (B-22)

Following the procedure for the preparation of compound B-6 but substituting (6-bromopyridin-2-yl)methanol for (5-trifluoromethyl-pyridin-2-yl)methanol provided compound B-22 (29.4%) as a white solid. $C_{23}H_{18}F_4N_4O$. LCMS: Rt 3.37, m/z 443 [M+H]$^+$ (method 7).

$^1$H NMR (400 MHz, CDCl$_3$) δ ppm 4.48 (dt, J=27.0, 4.6 Hz, 2H), 4.84 (dt, J=46.9, 4.6 Hz, 2H), 5.29 (s, 2H), 6.95-7.00 (m, 2H), 7.16-7.21 (m, 2H), 7.39-7.45 (m, 2H), 7.70 (d, J=6.5 Hz, 1H), 7.70 (s, 1H), 7.97 (dd, J=8.2, 2.0 Hz, 1H), 8.46-8.53 (m, 2H), 8.86 (br. s, 1H).

5-cyclopropyl-2-[[4-[1-(2-fluoroethyl)-4-(4-pyridinyl)-1H-pyrazol-3-yl]phenoxy]methyl]-pyridine (B-23)

Following the procedure for the preparation of compound B-4, but substituting (5-methoxypyridin-2-yl)methanol for (5-cyclopropyl-pyridin-2-yl)methanol provided compound B-23 as a colourless oil that solidified on standing. Finally the compound was washed with diisopropyl ether to yield final compound B-23 (45.6%) as a white solid. $C_{25}H_{23}FN_4O$. LCMS: Rt 3.24, m/z 415 [M+H]$^+$ (method 7).

$^1$H NMR (500 MHz, CDCl$_3$) δ ppm 0.67-0.78 (m, 2H), 0.96-1.10 (m, 2H), 1.87-1.95 (m, 1H), 4.47 (dt, J=26.9, 4.8 Hz, 2H), 4.84 (dt, J=47.1, 4.7 Hz, 2H), 5.19 (s, 2H), 6.94-6.99 (m, 2H), 7.16-7.21 (m, 2H), 7.32 (dd, J=8.1, 2.3 Hz, 1H), 7.36-7.41 (m, 3H), 7.70 (s, 1H), 8.40 (d, J=2.0 Hz, 1H), 8.48 (br. d, J=6.1 Hz, 2H).

2-[[4-[1-(2-fluoroethyl)-4-(4-pyridinyl)-1H-pyrazol-3-yl]phenoxy]methyl]-6-methoxy-pyridine.succinate (B-24)

Following the procedure for the preparation of compound B-4 but substituting (5-methoxypyridin-2-yl)methanol for (6-methoxypyridin-2-yl)methanol provided compound B-24 that was converted into the corresponding succinic acid salt, in a similar way as it is described above for final compound B-3, which was crystallized from diethyl ether yielding the succinic acid salt of final compound B-24 (25.8%) as a white solid. $C_{23}H_{21}FN_4O_2 \cdot C_4H_6O_4$. LCMS: Rt 4.16, m/z 405 [M+H]$^+$ (method 2).

$^1$H NMR (500 MHz, DMSO-d$_6$) δ ppm 2.42 (s, 4H), 3.86 (s, 3H), 4.49 (dt, J=27.7, 4.9 Hz, 2H), 4.85 (dt, J=47.4, 4.9 Hz, 2H), 5.11 (s, 2H), 6.77 (d, J=8.4 Hz, 1H), 7.03-7.09 (m, 2H), 7.12 (d, J=7.2 Hz, 1H), 7.20-7.25 (m, 2H), 7.31-7.36 (m, 2H), 7.74 (dd, J=8.2, 7.4 Hz, 1H), 8.24 (s, 1H), 8.42-8.49 (m, 2H), 12.17 (br. s., 2H).

2-ethoxy-6-[[4-[1-(2-fluoroethyl)-4-(4-pyridinyl)-1H-pyrazol-3-yl]phenoxy]methyl]-pyridine.succinate (B-25)

Following the procedure for the preparation of compound B-4 but substituting (5-methoxypyridin-2-yl)methanol for (6-ethoxypyridin-2-yl)methanol provided compound B-25 that was converted into the corresponding succinic acid salt, in a similar way as it is described above for final compound B-3, which was crystallized from diethyl ether yielding the succinic acid salt of final compound B-25 (39.6%) as a white solid. $C_{24}H_{23}FN_4O_2 \cdot C_4H_6O_4$. LCMS: Rt 3.56, m/z 419 [M+H]$^+$ (method 7).

$^1$H NMR (400 MHz, DMSO-d$_6$) δ ppm 1.31 (t, J=6.9 Hz, 3H), 2.41 (s, 4H), 4.30 (q, J=7.2 Hz, 2H), 4.49 (dt, J=27.7, 4.6 Hz, 2H), 4.85 (dt, J=47.4, 4.9 Hz, 2H), 5.10 (s, 2H), 6.74 (d, J=8.3 Hz, 1H), 7.03-7.08 (m, 2H), 7.10 (d, J=7.2 Hz, 1H), 7.20-7.25 (m, 2H), 7.29-7.37 (m, 2H), 7.73 (dd, J=8.2, 7.3 Hz, 1H), 8.24 (s, 1H), 8.43-8.48 (m, 2H), 12.19 (br. s., 2H).

6-[[4-[1-(2-fluoroethyl)-4-(4-pyridinyl)-1H-pyrazol-3-yl]phenoxy]methyl]-2-pyridinecarbonitrile (B-26)

Following the procedure for the preparation of compound B-6 but substituting (6-bromopyridin-2-yl)methanol for 6-hydroxymethyl-2-cyanopyridine provided compound B-26 (40.8%) as a white solid after treatment with diethyl ether.

$C_{23}H_{18}FN_5O$. LCMS: Rt 2.68, m/z 400 [M+H]$^+$ (method 7).

$^1$H NMR (400 MHz, DMSO-d$_6$) δ ppm 4.50 (dt, J=27.5, 4.4 Hz, 2H), 4.85 (dt, J=47.4, 4.9 Hz, 2H), 5.28 (s, 2H), 7.05-7.10 (m, 2H), 7.23 (br. d, J=4.4 Hz, 2H), 7.33-7.38 (m, 2H), 7.89 (dd, J=7.9, 0.9 Hz, 1H), 8.03 (dd, J=7.6, 0.9 Hz, 1H), 8.13 (t, J=7.7 Hz, 1H), 8.24 (s, 1H), 8.47 (br. s., 2H).

3-bromo-2-[[4-[1-(2-fluoroethyl)-4-(4-pyridinyl)-1H-pyrazol-3-yl]phenoxy]methyl]-6-methoxy-pyridine (B-27)

Following the procedure for the preparation of compound B-6 but substituting (6-bromopyridin-2-yl)methanol for 3-bromo-2-(hydroxymethyl)-6-methoxypyridine provided final compound B-27 (54.1%) as a white solid. $C_{23}H_{20}BrFN_4O_2$. LCMS: Rt 4.58, m/z 483 [M+H]$^+$ (method 2).

$^1$H NMR (400 MHz, CDCl$_3$) δ ppm 3.85 (s, 3H), 4.47 (dt, J=26.8, 4.6 Hz, 2H), 4.84 (dt, J=46.9, 4.6 Hz, 2H), 5.22 (s, 2H), 6.61 (d, J=8.6 Hz, 1H), 6.98-7.03 (m, 2H), 7.17-7.21 (m, 2H), 7.36-7.41 (m, 2H), 7.68-7.72 (m, 2H), 8.46-8.51 (m, 2H).

2-[[4-[1-(2-fluoroethyl)-4-(4-pyridinyl)-1H-pyrazol-3-yl]phenoxy]methyl]-3,4,5-trimethyl-pyridine.succinate (B-28)

Following the procedure for the preparation of compound B-3 but substituting 3,5-dimethyl-2-hydroxymethylpyridine for (3,4,5-trimethylpyridin-2-yl)methanol provided final compound B-28 (56.8%) in its succinic acid salt form as a white solid.

$C_{25}H_{25}FN_4O \cdot C_4H_6O_4$. LCMS: Rt 3.53, m/z 417 [M+H]$^+$ (method 6).

$^1$H NMR (500 MHz, DMSO-d$_6$) δ ppm 2.26 (s, 3H), 2.30 (s, 3H), 2.35 (s, 3H), 2.48 (s, 4H), 4.55 (dt, J=27.7, 4.6 Hz, 2H), 4.91 (dt, J=47.1, 4.6 Hz, 2H), 5.23 (s, 2H), 7.09-7.14 (m, 2H), 7.27-7.31 (m, 2H), 7.35-7.41 (m, 2H), 8.21 (s, 1H), 8.28 (s, 1H), 8.50-8.54 (m, 2H), 12.22 (br. s., 2H).

In Vitro Assay

Rat recombinant PDE10A (rPDE10A) was expressed in Sf9 cells using a recombinant rPDE10A baculovirus construct. Cells were harvested after 48 h of infection and the rPDE10A protein was purified by metal chelate chromatography on Ni-sepharose 6FF. Tested compounds were dissolved and diluted in 100% DMSO to a concentration 100 fold of the final concentration in the assay. Compound dilutions (0.4 μl) were added in 384 well plates to 20 μl of incubation buffer (50 mM Tris pH 7.8, 8.3 mM MgCl2, 1.7 mM EGTA). 10 μl of rPDE10A enzyme in incubation buffer was added and the reaction was started by addition of 10 μl substrate to a final concentration of 60 nM cAMP and 0.008 μCi 3H-cAMP. The reaction was incubated for 60 minutes at room temperature. After incubation, the reaction was stopped with 20 μl of 17.8 mg/ml PDE SPA beads. After sedimentation of the beads during 30 minutes, the radioactivity was measured in a Perkin Elmer Topcount scintillation counter and results were expressed as cpm. For blanc values the enzyme was omitted from the reaction and replaced by incubation buffer. Control values were obtained by addition of a final concentration of 1% DMSO instead of compound. A best fit curve was fitted by a minimum sum of squares method to the plot of % of control value substracted with blanc value versus compound concentration and a pIC50 value was derived from this curve.

TABLE

Final compounds

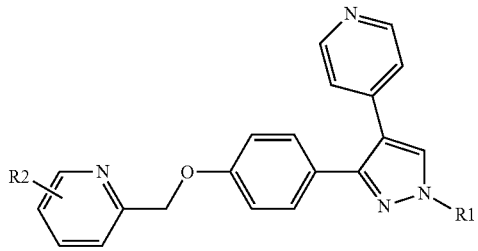

| Co. No. | R1 | R2 | Phys. data | Melting points °C. | pIC50 |
|---|---|---|---|---|---|
| B1 | CH$_2$CH$_2$F | 6-methyl | .2 HCl | 227.22 (DSC) | 8.6 |
| B2 | CH$_2$CH$_2$CH$_2$F | 6-methyl | .x HCl | 106.51 (DSC) | 7.7 |
| B3 | CH$_2$CH$_2$F | 3,5-dimethyl | .succinate | 138.81 (DSC) | 8.79 |
| B4 | CH$_2$CH$_2$F | 5-methoxy | Free base | 117.52 (DSC) | 8.48 |
| B5 | CH$_2$CF$_3$ | 5-methoxy | Free base | 136.3 | 8.29 |
| B6 | CH$_2$CH$_2$F | 6-bromo | .0.75 succinate | 108.78 (DSC) | 8.01 |
| B7 | CH$_2$CH$_2$F | 6-trifluoromethyl | Free base | | 6.96 |
| B8 | CH$_2$CH$_2$F | 6-cyclopropyl | .succinate | 91.25 (DSC) | 7.48 |
| B9 | CH$_2$CF$_3$ | 3-methoxy | Free base | 147.0 | 8.29 |
| B10 | CH$_2$CF$_3$ | 3-(2-fluoro ethoxy) | .succinate | 140.72 (DSC) | 8.2 |
| B11 | CH$_2$CF$_3$ | 5-(2-fluoroethoxy) | Free base | decomposed | 6.97 |
| B12 | CH$_2$CH$_2$CH$_2$F | 3-methoxy | Free base | 165.9 | 7.88 |
| B13 | CH$_2$CH$_2$CH$_2$F | 3-(2-fluoroethoxy) | .succinate | 118.38 (DSC) | 7.86 |
| B14 | CH$_2$CH$_2$CH$_2$F | 5-methoxy | .0.5 succinate | 126.64 (DSC) | 7.84 |
| B15 | CH$_2$CH$_2$CH$_2$F | 5-(2-fluoroethoxy) | Free base | 206.8 | 6.6 |
| B16 | CH$_2$CH$_2$F | 3-methoxy | .succinate | 178.95 (DSC) | 8.43 |
| B17 | CH$_2$CH$_2$F | 3-(2-fluoroethoxy) | .succinate | 114.18 (DSC) | 8.42 |
| B18 | CH$_2$CH$_2$F | 3-fluoro | .1.2 succinate | | 7.79 |
| B19 | CH$_2$CH$_2$F | 5-(2-fluoroethoxy) | Free base | 212.7 | 7 |
| B20 | CH$_2$CH$_2$F | 5-bromo | Free base | 125.8 | 8.02 |
| B21 | CH$_2$CH$_2$F | 5-cyano | Free base | decomposed | 7.1 |
| B22 | CH$_2$CH$_2$F | 5-trifluoromethyl | Free base | 133.23 (DSC) | 7.04 |
| B23 | CH$_2$CH$_2$F | 5-cyclopropyl | Free base | decomposed | 7.46 |
| B24 | CH$_2$CH$_2$F | 6-methoxy | .succinate | 113.25 (DSC) | 8.53 |
| B25 | CH$_2$CH$_2$F | 6-ethoxy | .succinate | 119.65 (DSC) | 7.68 |
| B26 | CH$_2$CH$_2$F | 6-cyano | Free base | 148.7 | 7.48 |
| B27 | CH$_2$CH$_2$F | 3-bromo-6-methoxy | Free base | 119.2 | 7.55 |
| B28 | CH$_2$CH$_2$F | 3,4,5-trimethyl | .succinate | 197.08 (DSC) | 8.36 |

C. Analytical Part

Melting Points:

Values are peak values, and are obtained with experimental uncertainties that are commonly associated with this analytical method.

For a number of compounds, noted as "DSC" in the above table, melting points were determined with a DSC823e (Mettler-Toledo). Melting points were measured with a temperature gradient of 30° C./minute. Maximum temperature was 400° C.

For a number of compounds, melting points were determined in open capillary tubes on a Mettler FP62 apparatus. Melting points were measured with a temperature gradient of 10° C./minute. Maximum temperature was 300° C. The melting point was read from a digital display.

Nuclear Magnetic Resonance (NMR)

$^1$H NMR spectra were recorded either on a Bruker DPX-400 or on a Bruker AV-500 spectrometer with standard pulse sequences, operating at 400 MHz and 500 MHz respectively. Chemical shifts (δ) are reported in parts per million (ppm) downfield from tetramethylsilane (TMS), which was used as internal standard.

LCMS-Methods:

For LCMS-characterization of the compounds of the present invention, the following methods were used.

General Procedure for HP 1100-MS Instruments (TOF or SQD)

The HPLC measurement was performed using an HP 1100 (Agilent Technologies) system comprising a pump (quaternary or binary) with degasser, an autosampler, a column oven, a diode-array detector (DAD) and a column as specified in the respective methods. The MS detector was configured with either an electrospray ionization source or an ESCI dual ionization source (electrospray combined with atmospheric pressure chemical ionization). Nitrogen was used as the nebulizer gas. The source temperature was maintained either at 140° C. or 100° C. Data acquisition was performed either with MassLynx-Openlynx software or Chemsation-Agilent Data Browser software.

General Procedure for Acquity-SQD Instrument

The UPLC (Ultra Performance Liquid Chromatography) measurement was performed using an Acquity UPLC (Waters) system comprising a sampler organizer, a binary pump with degasser, a four column's oven, a diode-array detector (DAD) and a column as specified in the respective methods. The MS detector was configured with an ESCI dual ionization source (electrospray combined with atmospheric pressure chemical ionization). Nitrogen was used as the nebulizer gas. The source temperature was maintained at 140° C. Data acquisition was performed with MassLynx-Openlynx software.

MS Procedure for LC Methods 1 and 2:

High-resolution mass spectra (Time of Flight, TOF detector) were acquired only in positive ionization mode or in positive/negative modes by scanning from 100 to 750 umas. The capillary needle voltage was 2.5 kV for positive mode 2.9 Kv for negative ionization mode. The cone voltage was 20 V for both positive and negative ionization modes. Leucine-Enkephaline was the standard substance used for the lock mass calibration.

MS Procedure for LC Methods 3, 4, 5, 6, 7 and 8:

Low-resolution mass spectra (single quadrupole, SQD detector) were acquired only in positive ionization mode or in positive/negative modes by scanning from 100 to 1000 umas. The capillary needle voltage was 3 kV. For positive ionization mode the cone voltage was 20V, 25V or 20V/50V. For negative ionization mode the cone voltage was 30V.

Method 1

In addition to the general procedure: Reversed phase HPLC was carried out on an XDB-C18 cartridge (1.8 μm, 2.1×30 mm) from Agilent, at 60° C. with a flow rate of 1 ml/min, at 60° C. The gradient conditions used are: 90% A (0.5 g/l ammonium acetate solution), 5% B (acetonitrile), 5% C (methanol) to 50% B and 50% C, then to 100% B and equilibrated to initial conditions up to 9.0 minutes run. Injection volume 2 μl.

Method 2

In addition to the general procedure: Reversed phase HPLC was carried out on a Sunfire-C18 column (2.5 µm, 2.1×30 mm) from Waters, with a flow rate of 1.0 ml/min, at 60° C. The gradient conditions used are: 95% A (0.5 g/l ammonium acetate solution+5% of acetonitrile), 5% B (acetonitrile or acetonitrile/methanol 1/1), to 100% B and equilibrated to initial conditions up to 9 or 7 minutes run. Injection volume 2 µl.

Method 3

In addition to the general procedure: Reversed phase HPLC was carried out on a XDB-C18 cartridge (1.8 µm, 2.1×30 mm) from Agilent, with a flow rate of 0.8 ml/min, at 60° C. The gradient conditions used are: 90% A (0.5 g/l ammonium acetate solution), 10% B (mixture of Acetonitrile/Methanol, 1/1), to 100% B and equilibrated to initial conditions up to 9.0 minutes run. Injection volume 2 µl.

Method 4

In addition to the general procedure: Reversed phase HPLC was carried out on a Sunfire-C18 column (2.5 µm, 2.1×30 mm) from Waters, with a flow rate of 1.0 ml/min, at 60° C. The gradient conditions used are: 95% A (0.5 g/l ammonium acetate solution+5% acetonitrile), 5% B (mixture of acetonitrile/methanol, 1/1), to 100% B and equilibrated to initial conditions up to 7 minutes run. Injection volume 2 µl.

Method 5

In addition to the general procedure: Reversed phase HPLC was carried out on a XBridge-C18 column (2.5 µm, 2.1×30 mm) from Waters, with a flow rate of 1.0 ml/min, at 60° C. The gradient conditions used are: 95% A (0.5 g/l ammonium acetate solution+5% acetonitrile), 5% B (mixture of acetonitrile/methanol, 1/1), to 100% B and equilibrated to initial conditions up to 9.0 minutes run. Injection volume 2 µl.

Method 6

In addition to the general procedure: Reversed phase HPLC was carried out on an Eclipse Plus-C18 column (3.5 µm, 2.1×30 mm) from Agilent, with a flow rate of 1.0 ml/min, at 60° C. The gradient conditions used are: 95% A (0.5 g/l ammonium acetate solution+5% acetonitrile), 5% B (acetonitrile or mixture of acetonitrile/methanol, 1/1), to 100% B and equilibrated to initial conditions up to 7 minutes run. Injection volume 2 µl.

Method 7

In addition to the general procedure: Reversed phase UPLC was carried out on a BEH-C18 column (1.7 µm, 2.1×50 mm) from Waters, with a flow rate of 0.8 ml/min, at 60° C. The gradient conditions used are: 95% A (0.5 g/l ammonium acetate solution+5% acetonitrile), 5% B (mixture of acetonitrile/methanol, 1/1), to 20% A, 80% B, then to 100% B and equilibrated to initial conditions up to 7 or 5 minutes run. Injection volume 0.5 µl.

Method 8

In addition to the general procedure: Reversed phase UPLC was carried out on a BEH-C18 column (1.7 µm, 2.1×50 mm) from Waters, with a flow rate of 1.0 ml/min, at 50° C. The gradient conditions used are: 95% A (0.5 g/l ammonium acetate solution+5% acetonitrile), 5% B (acetonitrile), to 40% A, 60% B, then to 5% A, 95% B and equilibrated to initial conditions up to 5 minutes run. Injection volume 0.5 µl.

II. Biodistribution Studies:

General Method

Biodistribution studies were carried out in healthy male Wister rats (body weight 200-500 g) at 2 min, 30 min and 60 min post injection (p.i.) (n=3/time point). For [$^{18}$F]B-4 only the 2 min and 30 min time points were studied. Rats were injected with about 30 µCi of the tracer via tail vein under anesthesia (2.5% isoflurane in $O_2$ at 1 L/min flow rate) and sacrificed by decapitation at above specified time points. Blood and major organs were collected in tared tubes and weighed. The radioactivity in blood, organs and other body parts was measured using an automated gamma counter. The distribution of radioactivity in different parts of the body at different time points p.i. of the tracer was calculated and expressed as percentage of injected dose (% ID), and as percentage of injected dose per gram tissue (% ID/g) for the selected organs. % ID is calculated as cpm in organ/total cpm recovered. For calculation of total radioactivity in blood, blood mass was assumed to be 7% of the body mass.

A. Biodistribution Results for Compound [$^{18}$F]B-1

The results of the in vivo distribution study of [$^{18}$F]B-1 in male Wistar rats is presented in Tables 1 and 2. Table 1 shows the % ID values at 2 min, 30 min and 60 min p.i. of the radiotracer. At 2 min p.i. about 4.0% of the injected dose was present in the blood, and this cleared to 2.2% by 60 min after injection of the tracer. The total initial brain uptake of the tracer was 0.59%, with 0.49% of the ID in the cerebrum and 0.09% in the cerebellum. At 60 min after injection of the radiotracer, 54% ID was present in the liver and intestines. Because of its lipophilic character, the urinary excretion of the tracer was minimal with only ~2.6% ID present in the urinary system at 60 min p.i. Increasing accumulation in the stomach was observed (3% ID, 10% ID, 17% ID at respectively 2, 30 and 60 min p.i.) In view of the large mass of the carcass, significant amount of the injected dose (~28% ID) was present in the carcass at all time points examined. Typically, carcass constitutes to >90% of the total body weight of the animal. Table 2 shows the % ID/g values for different organs at 2 min, 30 min and 60 min p.i.

TABLE 1

Biodistribution of [$^{18}$F]B-1 in normal rats at 2, 30 and 60 min p.i.

| | % ID[a] | | |
|---|---|---|---|
| Organ | 2 min | 30 min | 60 min |
| Urine | 0.09 ± 0.1 | 0.29 ± 0.0 | 1.22 ± 0.2 |
| Kidneys | 4.24 ± 0.5 | 1.44 ± 0.2 | 1.38 ± 0.1 |
| Liver | 41.94 ± 2.2 | 45.29 ± 5.2 | 34.49 ± 8.0 |
| Spleen + Pancreas | 1.92 ± 0.2 | 0.57 ± 0.2 | 0.43 ± 0.1 |
| Lungs | 0.92 ± 0.2 | 0.42 ± 0.1 | 0.26 ± 0.1 |
| Heart | 0.60 ± 0.1 | 0.21 ± 0.0 | 0.16 ± 0.0 |
| Stomach | 3.09 ± 0.1 | 9.73 ± 1.7 | 16.74 ± 4.6 |
| Intestines | 10.79 ± 1.5 | 14.67 ± 3.3 | 19.61 ± 1.5 |
| Striatum | 0.036 ± 0.012 | 0.013 ± 0.001 | 0.006 ± 0.002 |
| Hippocampus | 0.018 ± 0.004 | 0.006 ± 0.000 | 0.005 ± 0.001 |
| Cortex | 0.069 ± 0.008 | 0.026 ± 0.004 | 0.018 ± 0.004 |
| Rest of cerebrum | 0.367 ± 0.054 | 0.127 ± 0.010 | 0.116 ± 0.027 |
| Cerebrum total | 0.490 ± 0.067 | 0.172 ± 0.012 | 0.145 ± 0.032 |
| Cerebellum | 0.091 ± 0.018 | 0.028 ± 0.000 | 0.023 ± 0.005 |
| Blood | 3.96 ± 0.5 | 2.40 ± 0.4 | 2.16 ± 0.4 |
| Carcass | 33.12 ± 2.3 | 25.50 ± 2.1 | 23.68 ± 3.9 |

Data are expressed as mean ± SD;
n = 3 per time point;
[a]Percentage of injected dose calculated as cpm in organ/total cpm recovered

TABLE 2

[$^{18}$F]B-1 concentration in different organs at 2, 30 and 60 min p.i.

| | % ID/g[a] | | |
|---|---|---|---|
| Organ | 2 min | 30 min | 60 min |
| Kidneys | 1.75 ± 0.24 | 0.61 ± 0.11 | 0.46 ± 0.02 |
| Liver | 3.40 ± 0.31 | 3.72 ± 0.87 | 2.53 ± 0.23 |
| Spleen + Pancreas | 1.47 ± 0.15 | 0.39 ± 0.04 | 0.26 ± 0.07 |
| Lungs | 0.69 ± 0.34 | 0.27 ± 0.04 | 0.16 ± 0.05 |

TABLE 2-continued

[$^{18}$F]B-1 concentration in different organs at 2, 30 and 60 min p.i.

| | % ID/g$^a$ | | |
|---|---|---|---|
| Organ | 2 min | 30 min | 60 min |
| Heart | 0.76 ± 0.09 | 0.24 ± 0.03 | 0.15 ± 0.04 |
| Striatum | 0.648 ± 0.075 | 0.250 ± 0.029 | 0.162 ± 0.042 |
| Hippocampus | 0.307 ± 0.041 | 0.096 ± 0.012 | 0.074 ± 0.050 |
| Cortex | 0.734 ± 0.148 | 0.204 ± 0.016 | 0.113 ± 0.031 |
| Rest of cerebrum | 0.411 ± 0.023 | 0.138 ± 0.013 | 0.107 ± 0.030 |
| Cerebrum total | 0.444 ± 0.026 | 0.148 ± 0.014 | 0.105 ± 0.035 |
| Cerebellum | 0.607 ± 0.019 | 0.145 ± 0.020 | 0.079 ± 0.021 |
| Blood | 0.21 ± 0.02 | 0.12 ± 0.01 | 0.10 ± 0.02 |
| Cerebrum + Cerebellum | 0.47 ± 0.03 | 0.15 ± 0.02 | 0.10 ± 0.03 |

Data are expressed as mean ± SD;
n = 3 per time point;
$^a$% ID/g values are calculated as % ID/weight of the organ in g As kidneys and liver are the excretory organs, they have the highest % ID/g values with about 1.8% ID/g for kidneys and 3.4% ID/g for liver at 2 min p.i. The % ID/g values for different regions of brain, namely striatum, hippocampus, cortex and cerebellum are presented in Table 2. In order to correct for differences in body weight between different animals, the % ID/g tissue values were normalized for body weight. The normalized values are presented in Table 3. For all studied brain regions there is a significant decrease in radioactivity concentration from 2 to 30 min (≤0.07% ID/g corrected for body weight at 30 min p.i.), indicating significant washout of the tracer from all studied brain regions.

TABLE 3

[$^{18}$F]B-1 concentration in different organs at 2, 30 and 60 min p.i. normalized for the body weight of the animal

| | % ID/g × body wt. in kg$^a$ | | |
|---|---|---|---|
| Organ | 2 min | 30 min | 60 min |
| Kidneys | 0.47 ± 0.05 | 0.17 ± 0.01 | 0.15 ± 0.01 |
| Liver | 0.92 ± 0.05 | 1.02 ± 0.13 | 0.81 ± 0.13 |
| Spleen + Pancreas | 0.40 ± 0.03 | 0.11 ± 0.02 | 0.08 ± 0.02 |
| Lungs | 0.19 ± 0.08 | 0.08 ± 0.02 | 0.05 ± 0.02 |
| Heart | 0.21 ± 0.02 | 0.07 ± 0.01 | 0.05 ± 0.01 |
| Striatum | 0.175 ± 0.02 | 0.070 ± 0.01 | 0.051 ± 0.01 |
| Hippocampus | 0.083 ± 0.01 | 0.027 ± 0.01 | 0.023 ± 0.02 |
| Cortex | 0.199 ± 0.04 | 0.057 ± 0.01 | 0.036 ± 0.01 |
| Rest of cerebrum | 0.111 ± 0.00 | 0.039 ± 0.01 | 0.034 ± 0.01 |
| Cerebrum total | 0.120 ± 0.01 | 0.042 ± 0.01 | 0.033 ± 0.01 |
| Cerebellum | 0.164 ± 0.01 | 0.041 ± 0.01 | 0.025 ± 0.01 |
| Blood | 0.06 ± 0.01 | 0.03 ± 0.01 | 0.03 ± 0.01 |
| Cerebrum + Cerebellum | 0.13 ± 0.01 | 0.04 ± 0.01 | 0.03 ± 0.01 |

Data are expressed as mean ± SD;
n = 3 per time point;
$^a$% ID/g values are calculated as % ID/weight of the organ in g Table 4 shows the 2 min/30 min and 2 min/60 min ratios of % ID/g values (normalized for body weight of the animal) for different regions of the brain. For all brain regions the 2 min/30 min ratios are ≥2.49 indicating that the tracer already started to washout during this time period. Slowest washout is observed for striatum, the region with the highest expression of PDE10.

TABLE 4

Clearance of [$^{18}$F]B-1 from different regions of the brain calculated as 2 min-to-30 min and 2 min-to-60 min ratio for % ID/g values (normalized for body weight)

| Brain region | 2 min/30 min | 2 min/60 min |
|---|---|---|
| Striatum | 2.49 | 3.41 |
| Hippocampus | 3.06 | 3.63 |
| Cortex | 3.47 | 5.55 |
| Rest of cerebrum | 2.86 | 3.29 |
| Cerebrum total | 2.88 | 3.60 |
| Cerebellum | 4.01 | 6.60 |
| Blood | 1.65 | 1.83 |

Table 5 presents the ratios between striatum and other regions of the brain as well as blood at different time points post injection of [$^{18}$F]B-1. Striatum is considered as the PDE10A-rich region and cerebellum as the reference region. Therefore high striatum-to-cerebellum ratios are desired in order to have good quality images in vivo. The maximum striatum-to-cerebellum ratio was about 2, which is rather low for a good PDE10 imaging tracer.

The results of these biodistribution studies indicate that there is no significant retention of [$^{18}$F]B-1 in the PDE10A-rich region striatum.

TABLE 5

Striatum-to-other brain region ratios (calculated from % ID/g values normalized for body weight of the animal) at 2 min, 30 min and 60 min p.i. of [$^{18}$F]B-1

| Brain region | 2 min | 30 min | 60 min |
|---|---|---|---|
| striatum/hippocampus | 2.11 | 2.59 | 2.24 |
| striatum/cortex | 0.88 | 1.22 | 1.43 |
| striatum/cerebellum | 1.07 | 1.72 | 2.06 |
| striatum/blood | 3.10 | 2.05 | 1.66 |

B. Biodistribution Results for Compound [$^{18}$F]B-3

The results of the in vivo distribution study of [$^{18}$F]B-3 in male Wistar rats is presented in Tables 6 and 7. Table 6 shows the % ID values at 2 min, 30 min and 60 min p.i. of the radiotracer. The total initial brain uptake of the tracer was rather low: 0.39% of the ID at 2 min p.i., with 0.31% ID in the cerebrum and 0.07% ID in the cerebellum. At 30 min p.i. 0.035% of ID was present in striatum, which has the highest expression of PDE10A, and where the radiotracer is expected to show binding. Clearance from blood circulation was rather slow. At 2 min p.i. about 4.0% of the injected dose was present in the blood, and this cleared to 3.3% by 60 min p.i. The tracer was cleared mainly by the hepatobiliary system as there was in total 50% of ID present in liver and intestines 60 min after injection of the radiotracer. Because of its lipophilic character, the urinary excretion of the tracer was minimal with only ~3.2% ID present in the urinary system at 60 min p.i. There is also an unexpected high accumulation in the stomach (2.6% ID, 6.7% ID, 20% ID at respectively 2, 30 and 60 min p.i.). In view of the large mass of the carcass, significant amount of the injected dose (~27% ID) was present in the carcass at all time points examined Typically, carcass constitutes to >90% of the total body weight of the animal.

Table 7 shows the % ID/g values for different organs at 2 min, 30 min and 60 min p.i.

TABLE 6

Biodistribution of [$^{18}$F]B-3 in normal rats at 2, 30 and 60 min p.i.

| | % ID$^a$ | | |
|---|---|---|---|
| Organ | 2 min | 30 min | 60 min |
| Urine | 0.17 ± 0.0 | 1.11 ± 0.2 | 1.69 ± 0.2 |
| Kidneys | 3.66 ± 0.6 | 1.22 ± 0.2 | 1.48 ± 0.0 |
| Liver | 47.78 ± 2.3 | 42.62 ± 1.5 | 30.31 ± 5.7 |
| Spleen + Pancreas | 1.01 ± 0.3 | 0.31 ± 0.1 | 0.31 ± 0.0 |
| Lungs | 0.72 ± 0.1 | 0.47 ± 0.1 | 0.38 ± 0.1 |
| Heart | 0.39 ± 0.0 | 0.18 ± 0.0 | 0.18 ± 0.0 |
| Stomach | 2.55 ± 0.4 | 6.70 ± 1.2 | 19.96 ± 3.9 |
| Intestines | 8.78 ± 1.0 | 21.48 ± 2.5 | 19.44 ± 2.8 |
| Striatum | 0.023 ± 0.006 | 0.035 ± 0.006 | 0.030 ± 0.006 |
| Hippocampus | 0.011 ± 0.002 | 0.006 ± 0.001 | 0.006 ± 0.002 |
| Cortex | 0.035 ± 0.010 | 0.019 ± 0.002 | 0.017 ± 0.002 |
| Rest of cerebrum | 0.236 ± 0.038 | 0.121 ± 0.025 | 0.115 ± 0.026 |
| Cerebrum total | 0.305 ± 0.049 | 0.180 ± 0.027 | 0.169 ± 0.032 |
| Cerebellum | 0.071 ± 0.016 | 0.026 ± 0.004 | 0.023 ± 0.009 |
| Blood | 3.98 ± 0.4 | 3.93 ± 0.4 | 3.34 ± 0.7 |
| Carcass | 32.20 ± 1.2 | 23.51 ± 2.0 | 24.04 ± 1.5 |

Data are expressed as mean ± SD;
n = 3 per time point;
$^a$Percentage of injected dose calculated as cpm in organ/total cpm recovered

TABLE 7

[$^{18}$F]B-3 concentration in different organs at 2, 30 and 60 min p.i.

| | % ID/g$^a$ | | |
|---|---|---|---|
| Organ | 2 min | 30 min | 60 min |
| Kidneys | 1.86 ± 0.27 | 0.61 ± 0.06 | 0.48 ± 0.02 |
| Liver | 5.52 ± 0.17 | 4.72 ± 0.16 | 2.44 ± 0.40 |
| Spleen + Pancreas | 1.09 ± 0.16 | 0.30 ± 0.05 | 0.20 ± 0.02 |
| Lungs | 0.58 ± 0.08 | 0.37 ± 0.07 | 0.24 ± 0.03 |
| Heart | 0.58 ± 0.11 | 0.24 ± 0.02 | 0.16 ± 0.02 |
| Striatum | 0.462 ± 0.059 | 0.575 ± 0.098 | 0.564 ± 0.156 |
| Hippocampus | 0.202 ± 0.033 | 0.095 ± 0.010 | 0.077 ± 0.015 |
| Cortex | 0.308 ± 0.038 | 0.122 ± 0.014 | 0.086 ± 0.020 |
| Rest of cerebrum | 0.281 ± 0.045 | 0.150 ± 0.014 | 0.123 ± 0.023 |
| Cerebrum total | 0.288 ± 0.042 | 0.166 ± 0.013 | 0.133 ± 0.023 |
| Cerebellum | 0.286 ± 0.064 | 0.107 ± 0.016 | 0.085 ± 0.030 |
| Blood | 0.27 ± 0.01 | 0.27 ± 0.02 | 0.15 ± 0.03 |
| Cerebrum + Cerebellum | 0.30 ± 0.08 | 0.16 ± 0.01 | 0.13 ± 0.02 |

Data are expressed as mean ± SD;
n = 3 per time point;
$^a$% ID/g values are calculated as % ID/weight of the organ in g As kidneys and liver are the excretory organs, they have the highest % ID/g values with about 1.9% ID/g for kidneys and 5.5% ID/g for liver at 2 min p.i. The % ID/g values for different regions of brain, namely striatum, hippocampus, cortex and cerebellum are presented in Table 7. In order to correct for differences in body weight between different animals, the % ID/g tissue values were normalized for body weight. The normalized values are presented in Table 8. At 2 min p.i. the highest radioactivity concentration in brain is observed in the striatum region (0.098% ID/g corrected for body weight) and this increases in time (0.121% ID/g corn at 30 min and 0.178% ID/g corr. at 60 min p.i.). This accumulation of radioactivity in striatum is consistent with the higher expression of the PDE10 enzyme in this region. For hippocampus, cortex and cerebellum, regions with minimal expression of PDE10A, the concentration at 30 min is decreased compared to the 2 min time point, indicating washout of the tracer from these brain regions. The slight increase at 60 min for these brain regions can be due to formation of radiometabolite(s) that enter the brain.

TABLE 8

[$^{18}$F]B-3 concentration in different organs at 2, 30 and 60 min p.i. normalized for the body weight of the animal

| | % ID/g × body wt. in kg$^a$ | | |
|---|---|---|---|
| Organ | 2 min | 30 min | 60 min |
| Kidneys | 0.39 ± 0.07 | 0.13 ± 0.01 | 0.15 ± 0.00 |
| Liver | 1.17 ± 0.07 | 1.00 ± 0.03 | 0.77 ± 0.13 |
| Spleen + Pancreas | 0.23 ± 0.04 | 0.06 ± 0.01 | 0.06 ± 0.01 |
| Lungs | 0.12 ± 0.02 | 0.08 ± 0.02 | 0.08 ± 0.01 |
| Heart | 0.12 ± 0.03 | 0.05 ± 0.01 | 0.05 ± 0.01 |
| Striatum | 0.098 ± 0.01 | 0.121 ± 0.02 | 0.178 ± 0.05 |
| Hippocampus | 0.043 ± 0.01 | 0.020 ± 0.00 | 0.024 ± 0.00 |
| Cortex | 0.066 ± 0.01 | 0.026 ± 0.00 | 0.027 ± 0.01 |
| Rest of cerebrum | 0.060 ± 0.01 | 0.032 ± 0.00 | 0.039 ± 0.01 |
| Cerebrum total | 0.061 ± 0.01 | 0.035 ± 0.00 | 0.042 ± 0.01 |
| Cerebellum | 0.061 ± 0.02 | 0.023 ± 0.00 | 0.027 ± 0.01 |
| Blood | 0.06 ± 0.01 | 0.06 ± 0.01 | 0.05 ± 0.01 |
| Cerebrum + Cerebellum | 0.06 ± 0.01 | 0.03 ± 0.01 | 0.04 ± 0.01 |

Table 9 shows 2 min/30 min and 2 min/60 min ratios of % ID/g values (normalized for body weight of the animal) for different regions of the brain. For the 2 min/30 min ratios, the cerebellum has the highest ratio of 2.71, indicating that the clearance of the tracer is the fastest from this region, followed by cortex (2.54) and hippocampus (2.14), regions with minimal expression of PDE10. For the striatum, on the other hand, the 2 min/60 min ratio (0.55) was lower than the 2 min/30 min ratio (0.81), indicating accumulation of [$^{18}$F]B-3 in the PDE10A-rich striatum.

TABLE 9

Clearance of [$^{18}$F]B-3 from different regions of the brain calculated as 2 min-to-30 min and 2 min-to-60 min ratio for % ID/g values (corrected for body weight of the animal)

| Brain region | 2 min/30 min | 2 min/60 min |
|---|---|---|
| Striatum | 0.81 | 0.55 |
| Hippocampus | 2.14 | 1.77 |
| Cortex | 2.54 | 2.39 |
| Rest of cerebrum | 1.90 | 1.53 |
| Cerebrum total | 1.75 | 1.45 |
| Cerebellum | 2.71 | 2.27 |
| Blood | 1.01 | 1.19 |

Table 10 presents the ratios between striatum and other regions of the brain as well as blood at different time points post injection of [$^{18}$F]B-3. Striatum is considered as the PDE10A-rich region and cerebellum as the reference region. Therefore high striatum-to-cerebellum ratios are desired in order to have good quality images in vivo. At 2 min p.i., the striatum-to-cerebellum ratio was about 1.6 and this ratio increased to 6.6 by 60 min after injection of the tracer. Striatum-to-cortex and striatum-to-hippocampus ratios were also ≥6.5 (60 min p.i.), confirming the specific retention of [$^{18}$F]B-3 in striatum.

TABLE 10

Striatum-to-other brain region ratios (calculated from % ID/g values normalized for body weight of the animal) at 2 min, 30 min and 60 min p.i. of [$^{18}$F]B-3

| Brain region | 2 min | 30 min | 60 min |
|---|---|---|---|
| striatum/hippocampus | 2.28 | 6.03 | 7.32 |
| striatum/cortex | 1.50 | 4.69 | 6.50 |
| striatum/cerebellum | 1.61 | 5.38 | 6.63 |
| striatum/blood | 1.73 | 2.16 | 3.74 |

The results from these biodistribution studies indicate that although the initial brain uptake was rather low, there is a continuous accumulation of [$^{18}$F]B-3 in striatum, while there is a washout in time from the reference region cerebellum. This suggests specific retention of [$^{18}$F]B-3 in the PDE10A-rich region striatum.

C. Biodistribution Results for Compound [$^{18}$F]B-4

The results of the in vivo distribution study of [$^{18}$F]B-4 in male Wistar rats is presented in Tables 11 and 12. Because of the rather low initial brain uptake and poor accumulation in striatum, the 60 min biodistribution analysis was not performed. Table 11 shows the % ID values at 2 min and 30 min p.i. of the radiotracer. The total initial brain uptake of the tracer was rather low: 0.40% of the ID at 2 min p.i., with 0.32% ID in the cerebrum and 0.07% ID in the cerebellum. At 30 min p.i. 0.019% of ID was present in striatum, which is rather low since the striatum has the highest expression of PDE10A, and in this region of the brain the radiotracer is expected to show binding. The tracer was cleared mainly via the liver (47% ID at 30 min p.i.) into the intestines (12% ID at 30 min p.i.) Because of its lipophilic character, the urinary excretion of the tracer was minimal with only ~2.5% ID present in the urinary system at 30 min p.i. There is also an unexpected high accumulation in the stomach (2.8% ID and 8% ID at respectively 2 and 30 min p.i.). Table 12 shows the % ID/g values for different organs at 2 min and 30 min p.i.

TABLE 11

Biodistribution of [$^{18}$F]B-4 in normal rats at 2 and 30 min p.i.

| | % ID$^a$ | |
|---|---|---|
| Organ | 2 min | 30 min |
| Urine | 0.28 ± 0.1 | 0.75 ± 0.1 |
| Kidneys | 4.99 ± 0.2 | 1.71 ± 0.3 |
| Liver | 35.98 ± 3.1 | 47.40 ± 3.5 |
| Spleen + Pancreas | 2.37 ± 0.2 | 0.56 ± 0.1 |
| Lungs | 1.12 ± 0.0 | 0.35 ± 0.1 |
| Heart | 0.62 ± 0.2 | 0.28 ± 0.1 |
| Stomach | 2.80 ± 0.2 | 8.08 ± 3.7 |
| Intestines | 12.02 ± 2.1 | 11.98 ± 1.9 |
| Striatum | 0.018 ± 0.003 | 0.019 ± 0.003 |
| Hippocampus | 0.006 ± 0.002 | 0.004 ± 0.000 |
| Cortex | 0.036 ± 0.007 | 0.022 ± 0.002 |
| Rest of cerebrum | 0.257 ± 0.014 | 0.162 ± 0.030 |
| Cerebrum total | 0.317 ± 0.014 | 0.208 ± 0.027 |
| Cerebellum | 0.065 ± 0.011 | 0.028 ± 0.002 |
| Blood | 4.55 ± 0.4 | 3.35 ± 0.5 |
| Carcass | 36.93 ± 1.3 | 26.15 ± 1.2 |

Data are expressed as mean ± SD;
n = 3 per time point;
$^a$Percentage of injected dose calculated as cpm in organ/total cpm recovered

TABLE 12

[$^{18}$F]B-4 concentration in different organs at 2 and 30 min p.i.

| | % ID/g$^a$ | |
|---|---|---|
| Organ | 2 min | 30 min |
| Kidneys | 1.34 ± 0.35 | 0.68 ± 0.12 |
| Liver | 2.32 ± 0.28 | 3.85 ± 0.04 |
| Spleen + Pancreas | 1.17 ± 0.03 | 0.40 ± 0.02 |
| Lungs | 0.46 ± 0.07 | 0.24 ± 0.02 |
| Heart | 0.45 ± 0.13 | 0.24 ± 0.04 |
| Striatum | 0.467 ± 0.002 | 0.458 ± 0.041 |
| Hippocampus | 0.193 ± 0.031 | 0.108 ± 0.013 |
| Cortex | 0.355 ± 0.012 | 0.145 ± 0.026 |
| Rest of cerebrum | 0.248 ± 0.030 | 0.149 ± 0.019 |
| Cerebrum total | 0.263 ± 0.029 | 0.157 ± 0.019 |
| Cerebellum | 0.231 ± 0.031 | 0.104 ± 0.005 |
| Blood | 0.14 ± 0.04 | 0.18 ± 0.03 |
| Cerebrum + Cerebellum | 0.269 ± 0.066 | 0.151 ± 0.016 |

Data are expressed as mean ± SD;
n = 3 per time point;
$^a$% ID/g values are calculated as % ID/weight of the organ in g As kidneys and liver are the excretory organs, they have the highest % ID/g values with about 1.3% ID/g for kidneys and 2.3% ID/g for liver at 2 min p.i. The % ID/g values for different regions of brain, namely striatum, hippocampus, cortex and cerebellum are presented in Table 12. In order to correct for differences in body weight between different animals, the % ID/g tissue values were normalized for body weight. The normalized values are presented in Table 13. At 2 min p.i. the highest radioactivity concentration in brain is observed in striatum (0.226% ID/g corrected for body weight). For hippocampus, cortex and cerebellum this value was respectively 0.091% ID/g corr., 0.168% ID/g corr., 0.109% ID/g corr. At 30 min p.i. the concentration in striatum decreased to 0.125% ID/g corrected for body weight. For the other brain regions the washout was higher (≤0.040% ID/g corrected for body weight at 30 min p.i.).

TABLE 13

[$^{18}$F]B-4 concentration in different organs at 2 and 30 min p.i. normalized for the body weight of the animal

| | % ID/g × body wt. in kg$^a$ | |
|---|---|---|
| Organ | 2 min | 30 min |
| Kidneys | 0.63 ± 0.17 | 0.19 ± 0.03 |
| Liver | 1.09 ± 0.08 | 1.05 ± 0.03 |
| Spleen + Pancreas | 0.55 ± 0.03 | 0.11 ± 0.01 |
| Lungs | 0.22 ± 0.03 | 0.07 ± 0.00 |
| Heart | 0.21 ± 0.06 | 0.07 ± 0.01 |
| Striatum | 0.226 ± 0.01 | 0.125 ± 0.01 |
| Hippocampus | 0.091 ± 0.01 | 0.029 ± 0.00 |
| Cortex | 0.168 ± 0.00 | 0.040 ± 0.01 |
| Rest of cerebrum | 0.117 ± 0.01 | 0.041 ± 0.00 |
| Cerebrum total | 0.124 ± 0.01 | 0.043 ± 0.00 |
| Cerebellum | 0.109 ± 0.01 | 0.029 ± 0.00 |
| Blood | 0.07 ± 0.01 | 0.05 ± 0.01 |
| Cerebrum + Cerebellum | 0.13 ± 0.01 | 0.04 ± 0.00 |

Table 14 shows 2 min/30 min and 2 min/60 min ratios of % ID/g values (normalized for body weight) for different regions of the brain. For the 2 min/30 min ratios, the cortex has the highest ratio of 4.24, indicating that the clearance of the tracer is fastest from this region, followed by cerebellum (3.82) and hippocampus (3.08), which do not express PDE10. For the striatum, the 2 min/30 min ratio was the lowest (1.80), indicating slower washout of [$^{18}$F]B-4 from the PDE10-rich region striatum.

TABLE 14

Clearance of [$^{18}$F]B-4 from different regions of the brain calculated as 2 min-to-30 min ratio for % ID/g values normalized for body weight of the animal

| Brain region | 2 min/30 min |
| --- | --- |
| Striatum | 1.80 |
| Hippocampus | 3.08 |
| Cortex | 4.24 |
| Rest of cerebrum | 2.87 |
| Cerebrum total | 2.90 |
| Cerebellum | 3.82 |
| Blood | 1.36 |

Table 15 presents the ratios between striatum and other regions of the brain as well as blood at different time points post injection of [$^{18}$F]B-4. Striatum is considered as the PDE10A-rich region and cerebellum as the reference region. Therefore high striatum-to-cerebellum ratios are desired in order to have good quality images in vivo. At 2 min p.i., the striatum-to-cerebellum ratio was about 2.07 and this ratio increased to 4.38 by 30 min after injection of the tracer. Striatum-to-cortex and striatum-to-hippocampus ratios were also >3.16, confirming retention of [$^{18}$F]B-4 in striatum.

TABLE 15

Striatum-to-other brain region ratios (calculated from % ID/g values normalized for body weight of the animal) at 2 min and 30 min p.i. of [$^{18}$F]B-4

| Brain region | 2 min | 30 min |
| --- | --- | --- |
| striatum/hippocampus | 2.49 | 4.25 |
| striatum/cortex | 1.35 | 3.16 |
| striatum/cerebellum | 2.07 | 4.38 |
| striatum/blood | 3.47 | 2.61 |

III. Radiometabolite Analysis of Compound [$^{18}$F]B-3
A. Plasma Radiometabolite Analysis at 2/30/60 Minutes p.i.

The metabolic stability of compound [$^{18}$F]B-3 was studied in normal rats (n=2) by determination of the relative amounts of parent tracer and radiometabolites in plasma at 2, 30 and 60 min p.i. of the tracer. After intravenous (i.v.) administration of about 1.7 mCi [$^{18}$F]B-3 via tail vein under anesthesia (2.5% isoflurane in $O_2$ at 1 L/min flow rate), blood was collected via the tail vein at the above mentioned time points (from the same animal) in lithium heparin containing tubes (4.5 mL LH PST tubes; BD vacutainer, BD, Franklin Lakes, USA) and stored on ice to stop the metabolism. Next, the blood was centrifuged for 10 min at 3000 rpm to separate the plasma. A volume of about 0.1 mL of plasma sample was isolated and spiked with about 10 µL of authentic non-radioactive B-3 (1 mg/mL solution) and 10 µL of intermediate I-7 (1 mg/mL solution, major metabolite according to in vitro studies) for identification. The plasma was then injected onto an HPLC system consisting of a Chromolith Performance column ($C_{18}$, 3 mm×100 mm, Merck) that was eluted with mixtures of 0.05 M NaOAc pH 5.5 (solvent A) and acetonitrile (solvent B). The following method was used for the analysis: isocratic elution with 100% A for 4 min at a flow rate of 0.5 mL/min, then linear gradient to 90% B by 14 min at a flow rate of 1 mL/min, and isocratic elution with a mixture of 10% A and 90% B at a flow rate of 1 mL/min until 17 min. After passing through an in-line UV detector (254 nm), the HPLC eluate was collected as 1-mL fractions (fraction collection each min) using an automatic fraction collector. For good separation between the intact tracer and the polar radiometabolite [$^{18}$F]I-7, fractions were collected each 30 sec starting from 8 min post HPLC injection until 12 min post HPLC injection. The radioactivity in all fractions was measured using an automated gamma counter. The peak corresponding to the intact [$^{18}$F]B-3 eluted at ~18 min, whereas the expected radiometabolite [$^{18}$F]I-7 eluted from ~13 to 15 min. An unidentified polar radiometabolite eluting from 3 to 5 min was also detected in brain. An overview of the results from the plasma radiometabolite analysis is presented in Table 16.

TABLE 16

Relative percentages of intact tracer and radiometabolites in rat plasma at 2, 30 and 60 min p.i. of [$^{18}$F]B-3. Results are presented as mean ± SD (n = 2)

| (%) | Mean ± SD (n = 2) | | |
| --- | --- | --- | --- |
| | 2 min | 30 min | 60 min |
| Polar metabolites | 3.7 ± 2.6 | 47.0 ± 4.1 | 61.6 ± 7.7 |
| Intact tracer | 96.3 ± 2.6 | 53.0 ± 4.1 | 38.4 ± 7.7 |

The analysis shows that at 2 min post injection of the radiotracer, about 96% of the recovered radioactivity in plasma was in the form of intact tracer. At 30 min p.i. 47% of polar radiometabolites were detected in plasma and this amount increased to 62% at 60 min p.i. The most polar radiometabolite probably arises from the cleavage and oxidation of the [$^{18}$F]fluoro-ethyl chain as this polar metabolite is also detected in brain (vide infra). The second polar radiometabolite, eluting closely to the intact tracer, could be identified as [$^{18}$F]I-7. The radioactivity corresponding to the (more lipophilic) fractions eluting after the intact tracer were negligible and this indicates no formation of lipophilic radiometabolites which, if present, could penetrate the blood-brain-barrier.

B. Perfused Brain Radiometabolite Analysis at 30/60 Minutes p.i.

For each studied time point two rats were injected with about 0.6 mCi of [$^{18}$F]B-3. At 30 min or 60 min after injection of the tracer, the rats were sacrificed by administering an overdose of Nembutal. When breathing had stopped, the rats were perfused with saline (Mini Plasco®, Braun, Melsungen, Germany) until the liver turned pale. Brain was isolated, cerebrum and cerebellum were separated and homogenized in 3 mL and 2 mL of acetonitrile, respectively, for about 2 min. A volume of 1 mL of this homogenate was diluted with an equal volume of water and a part of this homogenate was filtered through a 0.22 µm filter (Millipore, Bedford, USA). About 0.4 mL of the filtrate was diluted with 0.1 mL of water and spiked with 10 µL of authentic non-radioactive B-3 (1 mg/mL solution) and 10 µL of I-7 (1 mg/mL solution, major metabolite according to in vitro studies) for identification. The cerebrum/cerebellum homogenate was then injected onto an HPLC system consisting of an analytical XBridge™ column ($C_{18}$, 5 µM, 3 mm×100 mm, Waters) eluted with a mixture of 0.05 M sodium acetate buffer pH 5.5 and acetonitrile (70:30 v/v) at a flow rate of 0.8 mL/min. The HPLC eluate was collected as 1-mL fractions (fraction collection each minute) after passing through the UV detector, and the radioactivity in the fractions was measured using an automated gamma counter.

The peak corresponding to the intact [$^{18}$F]B-3 eluted at ~15 min, whereas the major radiometabolite [$^{18}$F]I-7 present in plasma was not detected in brain. The polar metabolite eluting around 2 min was also detected in plasma (vide supra) and passes the blood-brain-barrier as can be deduced from the in vitro incubation studies (vide infra). An overview of the results from the perfused rat brain radiometabolite analysis is presented in Table 17. The fraction of apolar radiometabolites detected in brain is negligible. The percentage of polar metabolite detected in cerebellum is higher compared to cerebrum. At 30 min p.i. about 86% of the recovered radioactivity was present as intact tracer in cerebrum, in cerebellum this was ~69%. After 60 min, the amount of intact tracer in cerebrum was decreased to ~72%, in cerebellum this was about 47%.

TABLE 17

Relative percentages of intact tracer and radiometabolites in perfused rat cerebrum and cerebellum at 30 and 60 min p.i. of [$^{18}$F]B-3.
Results are presented as mean ±SD (n = 2)

| (%) | 30 min p.i. | | 60 min p.i. | |
| --- | --- | --- | --- | --- |
|  | Cerebrum | Cerebellum | Cerebrum | Cerebellum |
| polar metabolite | 14.4 ± 10.1 | 30.6 ± 9.8 | 28.2 ± 7.9 | 53.0 ± 11.3 |
| intact tracer | 85.6 ± 10.1 | 69.4 ± 9.8 | 71.8 ± 7.9 | 47.0 ± 11.3 |

C. Radiometabolite Analysis of Rat Blood, Plasma and Brain Homogenate after in Vitro Incubation with [$^{18}$F]B-3 at 37° C. for 60 min Blood, plasma and homogenated brain of a rat were incubated with about 0.17 mCi of [$^{18}$F]B-3 at 37° C. After 60 min of incubation, the samples were put on ice to stop the metabolism. Blood and brain homogenate samples were prepared and analyzed onto RP-HPLC as described above. The amount of radiometabolites detected in rat blood, plasma and brain after one hour of incubation was negligable. This indicates that the polar radiometabolite (hypothesized to be a [$^{18}$F] fluoroethyl-derivative) observed in perfused rat cerebrum and cerebellum at 30 and 60 min p.i. of [$^{18}$F]B-3, is formed peripherally (in the liver) and crosses the blood-brain-barrier.

IV. MicroPET Imaging Studies

Imaging experiments were performed on a Focus™ 220 microPET scanner (Concorde Microsystems, Knoxville, Tenn., USA) using male Wistar rats with body weight varying between 300 and 600 g. During all scan sessions, animals were kept under gas anesthesia (2.5% isoflurane in $O_2$ at 1 L/min flow rate). Dynamic scans of 120 min were acquired in list mode. After reconstruction of the images, they were semi-automatically co-registered with a [$^{11}$C]raclopride template of the rat brain, and volumes of interest (VOIs) were generated for different anatomical brain structures (striatum, cerebral cortex and cerebellum) from which time-activity curves (TAC) were constructed for each individual image, using PMOD software (PMOD Technologies Ltd.). Normalization for body weight of the animal and injected dose was done. The radioactivity concentration in the different brain regions was expressed as SUV (standardized uptake value) as a function of time in seconds post injection of the radiotracer. The parametric binding potential (BP) values were calculated for all acquired images by using a simplified reference tissue model where the TAC of the cerebellum was used as input TAC for non-specific binding, using the same software (PMOD).

A. MicroPET Studies with Compound [$^{18}$F]B-3

Three rats were injected with about 2.2 mCi of high specific activity formulation of [$^{18}$F]B-3 via tail vein under anesthesia (2.5% isoflurane in $O_2$ at 1 L/min flow rate) and were scanned baseline for 2 hours.

High intensity signal was observed in the striatum with only background radioactivity in the cortical regions as well as in the cerebellum. The TACs show that after injection of [$^{18}$F]B-3 there is a high initial uptake of the radiotracer in the striatum, cortical regions and the cerebellum. After this initial high uptake due to the blood pool activity, the non-specific radioactivity cleared from the cortical regions and the cerebellum. In striatum, the radioactivity concentration reached its maximum (average SUV of 1.04) at about 16 min p.i. and this remained at a similar level until about 53 min p.i. Peak striatum-to-cerebellum ratios of 5.6 to 1 (n=3) were obtained at 23 min post injection and these ratios remained around 5.6 until about 53 min post injection. After this, the ratios decreased slowly until the end of the experiment due to the clearance of the activity from striatum. The BP value was calculated by using a simplified reference tissue model where TAC of the striata was considered as PDE10-rich TAC and TAC of the cerebellum was used as PDE10 poor TAC. The average BP at baseline was 4.1 (n=3).

Pretreatment studies where the non-radioactive analogue B-3 was administered via subcutaneous route at a dose of 2.5 mg/kg body weight were performed in one rat (one of the three animals that were used in the baseline scan). At 60 min after pretreatment, the rat was injected with 2.24 mCi of high specific activity formulation of [$^{18}$F]B-3 via tail vein under anesthesia (2.5% isoflurane in $O_2$ at 1 L/min flow rate) and a dynamic scan was performed for 2 hours.

When the animal was pre-treated with 'cold' compound, the striatum-to-cerebellum ratio decreased to 1.9. Also, there was about 80% reduction in BP values with pretreatment compared to baseline scans (BP after blocking=0.8 (n=1)).

Biodistribution studies as well as microPET imaging studies have shown specific retention or slower washout of this tracer from the PDE10-rich region striatum. Therefore, [$^{18}$F]B-3 is a suitable agent for imaging and quantification of PDE10A using PET.

B. MicroPET Baseline Study with Compound [$^{18}$F]B-4

One rat was injected with about 4 mCi of high specific activity formulation of [$^{18}$F]B-4 via tail vein under anesthesia (2.5% isoflurane in $O_2$ at 1 L/min flow rate) and was scanned baseline for 2 hours.

High intensity signal was observed in the striatum with only background radioactivity in the cortical regions as well as in the cerebellum. The TACs show that after injection of [$^{18}$F]B-4 there is a high initial uptake of the radiotracer in the striatum, cortical regions and the cerebellum. After this initial high uptake due to the blood pool activity, the non-specific radioactivity cleared from the cortical regions and the cerebellum. Clearance from striatum was slower, indicating retention of the tracer in this region. Peak striatum-to-cerebellum ratios of 4.4 to 1 were obtained at about 6 min post injection and these ratios remained around 4.4 until about 13 min post injection. After this, the ratio decreased rather fast due to the clearance of the activity from striatum. The BP value was calculated from these images by using a simplified reference tissue model where the cerebellum was used as a reference tissue. The BP at baseline was 2.5 (n=1).

Biodistribution studies as well as microPET imaging studies have shown specific retention or slower washout of [$^{18}$F]B-4 from the PDE10-rich region striatum. Compound [$^{18}$F]B-4 might also be a suitable agent for imaging of PDE10A expression in the brain using PET.

Comparison of the Kinetics of [$^{18}$F]B-3 and [$^{18}$F]Ref

The kinetics of two promising PDE10A PET ligands [$^{18}$F]B-3 and [$^{18}$F]Ref (2-{4-[1-(2-[$^{18}$F]fluoroethyl)-4-pyridin-4-yl-1H-pyrazol-3-yl]-phenoxymethyl}-quinoline WO-2010/097367) was compared.

Normal male Wistar rats were injected i.v. via the tail vein under anesthesia (2.5% isoflurane in $O_2$ at 1 L/min flow rate) with high specific activity tracer [$^{18}$F]B-3 or [$^{18}$F]Ref and scanned dynamically using μPET for 120 min. During the scan sessions, the animals were kept under gas anesthesia (2.5% isoflurane in $O_2$ at 1 L/min flow rate). The radioactivity concentration in the different brain regions was expressed as SUV value as a function of time p.i. of the radiotracer by normalization for body weight of the animal and injected dose.

Baseline Time-Activity Curves

For both tracers, there is a clear wash-out of radioactivity from cerebellum and cortex, brain regions where the expression of PDE10A is minimal Both tracers are retained in striatum, however the kinetics in this brain region is different for both PET ligands. [$^{18}$F]Ref reaches its maximum radioactivity concentration [average SUV of 0.73] at about 57 min p.i. and this stays at the same level until the end of the experiment. [$^{18}$F]B-3 reaches its maximum radioactivity concentration [average SUV of 1.04] at about 16 min p.i. Wash-out of [$^{18}$F]B-3 from striatum starts at about 53 min p.i. The faster kinetics of [$^{18}$F]B-3 compared to [$^{18}$F]Ref is also reflected in the striatum-to-cerebellum ratios. For [$^{18}$F]B-3 peak striatum-to-cerebellum ratios of about 5.6 were obtained at 23 min p.i. and these ratios remained around 5.6 until about 53 min p.i. After this, the ratios decreased slowly until the end of the experiment due to the clearance of the activity from striatum. For [$^{18}$F]Ref a maximum striatum-to-cerebellum ratio of 4.2 was reached after about 32 min p.i., which stayed constant until the end of the scan.

TABLE 18

Comparison of some kinetic parameters of [$^{18}$F]Ref and [$^{18}$F]B-3 at baseline.

|  | [$^{18}$F]Ref | [$^{18}$F]B-3 |
| --- | --- | --- |
| (SUV 100 min/SUV MAX)$_{striatum}$ | 1 | 0.7 |
| (time period of MAX SUV)$_{striatum}$ | ~57 min p.i.-end of scan | ~16 min-53 min p.i. |
| time period of MAX S/C ratio | ~32 min p.i.-end of scan | ~23 min-53 min p.i. |
| *MAX SUV in striatum | 0.7 | 1.0 |
| *MAX S/C ratio | 4.2 | 5.6 |

S/C = Striatum-to-cerebellum ratio.
*averaged values over time period of maximum Slower kinetics requires longer acquisition times in clinical applications to obtain robust distribution volume values. Therefore [$^{18}$F]B-3 is more promising as a PDE10A ligand for human brain imaging. In addition [$^{18}$F]B-3 reaches a higher radioactivity concentration in striatum and higher striatum-to-cerebellum ratios compared to [$^{18}$F]Ref (Table 18) resulting in higher quality in vivo images and more accurate quantification of the PDE10A binding potential.

The invention claimed is:

1. A compound of formula (I)

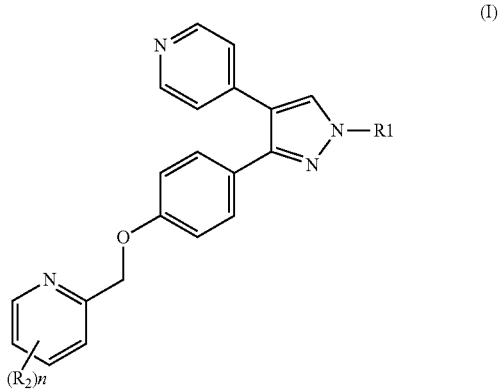

or a stereoisomeric form thereof, wherein
$R^1$ is 2-fluoroethyl, 2,2,2-trifluoroethyl or 3-fluoropropyl;
n is 1, 2 or 3;
each $R^2$ independently is $C_{1-3}$alkyl, cyclopropyl, $C_{1-3}$alkyloxy, halo$C_{1-3}$alkyloxy, halo, trifluoromethyl, trifluoromethoxy, difluoromethoxy, or cyano,
wherein at least one F is [$^{18}$F],
or a solvate or a salt form thereof.

2. The compound according to claim 1 wherein $R^1$ is 2-fluoroethyl.

3. The compound according to claim 1 wherein $R^2$ is 6-methyl, 3,5-dimethyl or 5-methoxy.

4. The compound according to claim 1 wherein the compound is 2-[[4-[1-(2-fluoroethyl)-4-(4-pyridinyl)-1H-pyrazol-3-yl]phenoxy]methyl]-3,5-dimethyl-pyridine succinate.

5. A sterile composition comprising a compound of Formula (I) as defined in claim 1 dissolved in saline.

6. A method of imaging a tissue, cells or a host, comprising contacting with or administering to a tissue, cells or a host a compound of Formula (I) as defined in claim 1, and imaging the tissue, cells or host with a positron-emission tomography imaging system.

7. A precursor compound of formula (VI)

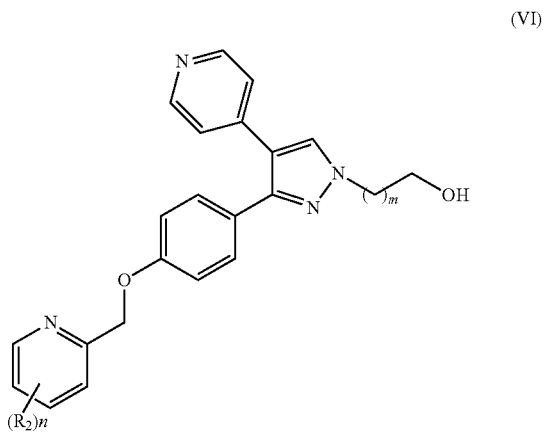

or a stereoisomeric form thereof, wherein
m is 1 or 2;
n is 1, 2 or 3;

each $R^2$ independently is $C_{1-3}$alkyl, cyclopropyl, $C_{1-3}$alkyloxy, $C_{1-3}$alkyloxy, halo, trifluoromethyl, trifluoromethoxy, difluoromethoxy, or cyano,
or a solvate or a salt form thereof.

* * * * *